(12) United States Patent
Brusilow et al.

(10) Patent No.: US 9,561,203 B2
(45) Date of Patent: Feb. 7, 2017

(54) USE OF METHIONINE SULFOXIMINE TO TREAT DISEASES CAUSED BY AN INFLAMMATORY CYTOKINE RESPONSE

(71) Applicants: William Brusilow, Grosse Pointe, MI (US); Paolo Bernardi, Padua (IT)

(72) Inventors: William Brusilow, Grosse Pointe, MI (US); Paolo Bernardi, Padua (IT)

( * ) Notice: Subject to any disclaimer, the term of this patent is extended or adjusted under 35 U.S.C. 154(b) by 0 days.

(21) Appl. No.: 14/833,543

(22) Filed: Aug. 24, 2015

(65) Prior Publication Data

US 2016/0081958 A1  Mar. 24, 2016

Related U.S. Application Data

(60) Division of application No. 14/021,653, filed on Sep. 9, 2013, now Pat. No. 9,119,821, which is a continuation of application No. 13/136,749, filed on Aug. 9, 2011, now Pat. No. 8,530,515.

(60) Provisional application No. 61/371,960, filed on Aug. 9, 2010, provisional application No. 61/486,810, filed on May 17, 2011.

(51) Int. Cl.
*A61K 31/198* (2006.01)

(52) U.S. Cl.
CPC .................................. *A61K 31/198* (2013.01)

(58) Field of Classification Search
CPC .................................................... A61K 31/198
USPC ........................................................ 514/562
See application file for complete search history.

(56) References Cited

U.S. PATENT DOCUMENTS

| | | | |
|---|---|---|---|
| 6,875,792 | B2 | 4/2005 | Brusilow et al. |
| 9,119,821 | B2 | 9/2015 | Brusilow et al. |
| 2004/0152778 | A1 | 8/2004 | Brusilow |
| 2005/0256196 | A1 | 11/2005 | Brusilow |
| 2009/0209474 | A1 | 8/2009 | Roegel et al. |

FOREIGN PATENT DOCUMENTS

WO   99/56767 A2   11/1999

OTHER PUBLICATIONS

Albrecht et al. Mini-review glutamine as a pathogenic factor in hepatic encephalopathy. Journal of Neuroscience Research 65:1-5 (2001).
Apte et al. Beta-catenin activation promotes liver regeneration after acetaminophen-induced injury. Am J Pathol Sep. 2009; 175(3): 1056-1065.
Armbrust and Ramadori. Functional characterization of two different Kupffer cell populations of normal rat liver. J Hepatol 1996; 25(4): 518-528.
Bernal et al. Acute liver failure. Lancet 2010; 376: 190-201.
Brusilow et al. Astrocyte glutamine synthetase: importance in hyperammonemic syndromes and potential target for therapy. Neurotherapeutics: The Journal of the American Society for Experimental NeuroTherapeutics Oct. 2010; 7: 452-470.
Brusilow. Hyperammonemic encephalopathy. Medicine 2002; 81(3): 240-249.
Bykov et al. Functional differences between periportal and perivenous Kupffer cells isolated by digitonin-collagenase perfusion. Comparative Hepatology 2004; 3(Suppl 1): S34.
Chen and Goeddel. TNF-R1 signaling: a beautiful pathway. Science May 31, 2002; 296: 1634-1635.
Crawford and Cohen. The essential role of L-glutamine in lymphocyte differentiation in vitro. J Cell Physiol 1985; 124(2): 275-282.
Decker and Keppler. Galactosamine hepatitis: key role of the nucleotide deficiency period in the pathogenesis of cell injury and cell death. Rev Physiol Biochem Pharmacol 1974; 71: 77-106.
Ding and Yin. Dissection of the multiple mechanisms of TNF-alpha-induced apoptosis in liver injury. J Cell Mol Med 2004; 8(4): 445-454.
Drew and Miners. The effects of buthionine sulphoximine (BSO) on glutathione depletion and xenobiotic biotransformation. Biochem Pharmacol 1984; 33(19):2989-2994.
Emoto et al. Increased resistance of LFA-1-deficient mice to lipopolysaccharide-induced shock/liver injury in the presence of TNF-alpha and IL-12 is mediated by IL-10: a novel role for LFA-1 in the regulation of the proinflammatory and anti-inflammatory cytokine balance. J Immunol 2003; 171(2): 584-593.
Freudenberg et al. Requirement for lipopolysaccharide-responsive macrophages in galactosamine-induced sensitization to endotoxin. Infect Immun Mar. 1986; 51(3): 891-895.
Galanos et al. Galactosamine-induced sensitization to the lethal effects of endotoxin. Proc Natl Acad Sci USA Nov. 1979; 76(11): 5939-5943.
Gebhardt and Mecke. Heterogeneous distribution of glutamine synthetase among rat liver parenchymal cells in situ and in primary culture. EMBO J 1983; 2(4): 567-570.
Ghoddoussi et al. Methionine sulfoximine, an inhibitor of glutamine synthetase, lowers brain glutamine and glutamate in a mouse model of ALS. J Neurol Sci 2010; 290(1-2): 41-47.
Gramaglia et al. Apoptosis to necrosis switching downstream of apoptosome formation requires inhibition of both glycolysis and oxidative phosphorylation in a BCL-X(L)- and PKB/AKT-independent fashion. Cell Death Differ 2004; 11(3): 342-353.
Griffith and Meister. Differential inhibition of glutamine and gamma-glutamylcysteine synthetases by alpha-alkyl analogs of methionine sulfoximine that induce convulsions. J Biol Chem Apr. 10, 1978; 253(7): 2333-2338.
Griffith and Meister. Potent and specific inhibition of glutathione synthesis by buthionine sulfoximine (S-n-butyl homocysteine sulfoximine). J Biol Chem Aug. 25, 1979; 254(16): 7558-7560.
Griffith and Meister. Selective inhibition of gamma-glutamyl-cycle enzymes by substrate analogs. Proc Natl Acad Sci USA 1977; 74(8): 3330-3334.

(Continued)

*Primary Examiner* — Jennifer M Kim
(74) *Attorney, Agent, or Firm* — Harness, Dickey & Pierce, P.L.C.

(57) ABSTRACT

Methods for treating or preventing an inflammatory response comprising administering a diastereomer or diastereomeric mixture of methionine sulfoximine (MSO). The MSO may be L-methionine S-sulfoximine (LSMSO), L-methionine R-sulfoximine (LRMSO), or diastereomeric mixture of LSMSO and LRMSO. Methods include those for treating liver failure associated with an inflammatory response.

17 Claims, 11 Drawing Sheets

(56) References Cited

OTHER PUBLICATIONS

Figure 1:
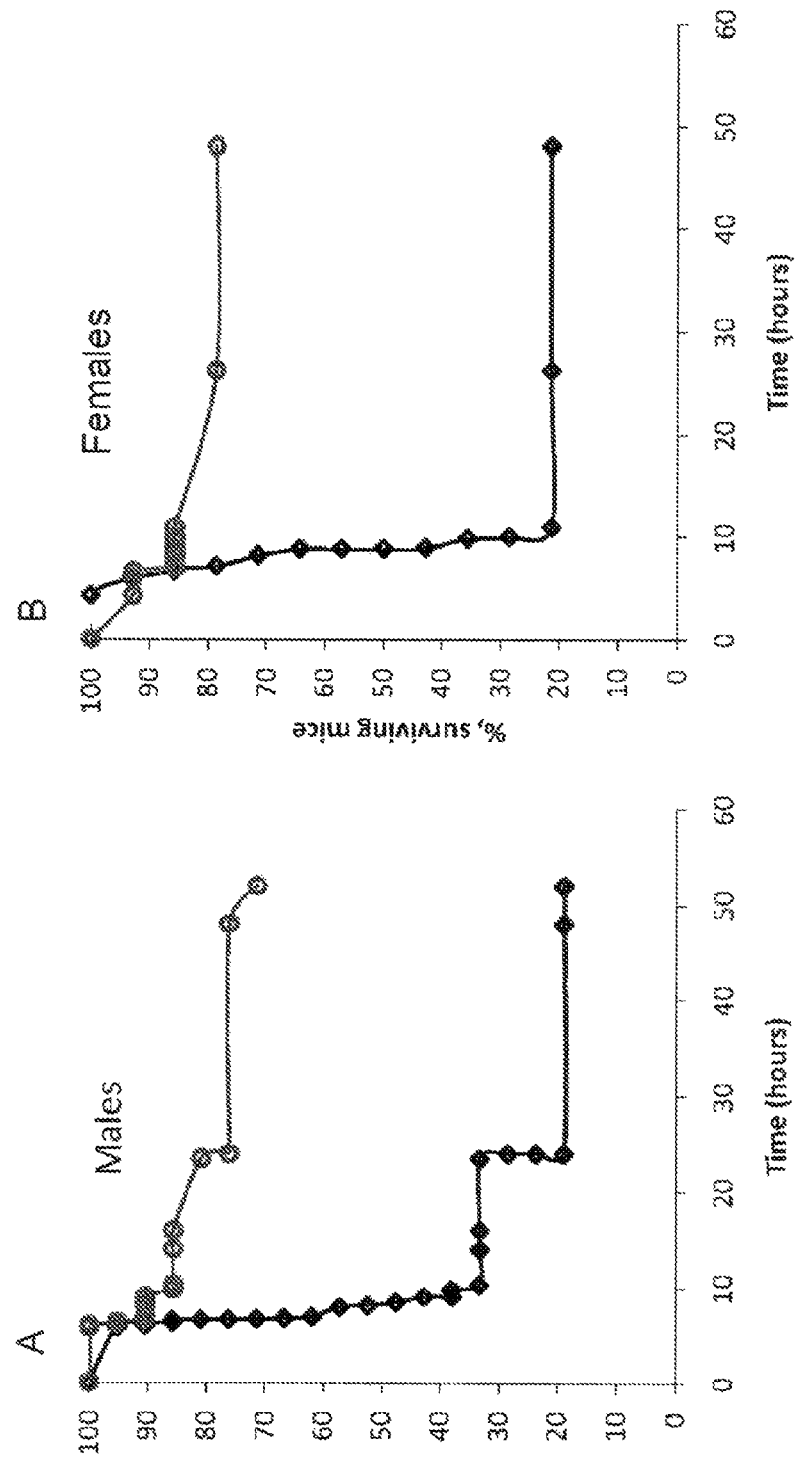

Griffith et al. Inhibition of glutathione biosynthesis by prothionine sulfoximine (S-n-propyl homocysteine sulfoximine), a selective inhibitor of gamma-glutamylcysteine synthetase. J Biol Chem Feb. 25, 1979; 254(4): 1205-1210.

Groeflin and Thoelen. Cerebral edema in the rat with galactosamine induced severe hepatitis. Experientia Apr. 28, 1978; 34(11): 1501-1503.

Haddad. L-Buthionine-(S,R)-sulfoximine, an irreversible inhibitor of gamma-glutamylcysteine synthetase, augments LPS-mediated pro-inflammatory cytokine biosynthesis: evidence for the implication of an IkappaB-alpha/NF-kappaB insensitive pathway. Eur Cytokine Netw Dec. 2001; 12(4): 614-624.

Haeussinger et al. Hepatocyte heterogeneity in glutamate metabolism and bidirectional transport in perfused rat liver. Eur J Biochem 1989; 185(1): 189-195.

Haeussinger et al. Interactions between glutamine metabolism and cell-volume regulation in perfused rat liver. Eur J Biochem 1990; 188(3): 689-695.

Hoedemakers et al. Heterogeneity in secretory responses of rat liver macrophages of different size. Liver 1995; 15(6): 313-319.

Hoerig et al. Exogenous glutamine requirement is confined to late events of T cell activation. J Cell Biochem 1993; 53(4): 343-351.

Horvath. The Jak-STAT pathway stimulated by interferon gamma. Sci STKE, Nov. 23, 2004; 2004 (260): tr8. DOI: 10.1126/stke.2602004tr8 (abstract).

Ide et al. Effects of gadolinium chloride (GdCl(3)) on the appearance of macrophage populations and fibrogenesis in thioacetamide-induced rat hepatic lesions. J Comp Pathol 2005; 133(2-3):92-102.

Jambekar et al. A glutamine synthetase inhibitor increases survival and decreases cytokine response in a mouse model of acute liver failure. Liver International 2011; 31: 1209-1221. DOI: 10.1111/j.1478-3231.2011.02553.x.

Kew et al. Dietary glutamine enhances murine T-lymphocyte responsiveness. J Nutr 1999; 129(8): 1524-1531.

Labow et al. Glutamine. World J. Surg 2000; 24(12): 1503-1513.

Leist and Jaeaettelae. Four deaths and a funeral: from caspases to alternative mechanisms. Nat Rev Mol Cell Biol Aug. 2001; 2(8): 589-598.

Leist et al. Cytokine-mediated hepatic apoptosis. Rev Physiol Biochem Pharmacol 1998; 133: 109-155.

Levy and Darnell, Jr. Stats: transcriptional control and biological impact. Nat Rev Mol Cell Biol Sep. 2002; 3(9): 651-662.

Li et al. Amino acids and immune function. Br J Nutr 2007; 98(2): 237-252.

Link. The cytokine storm in multiple sclerosis. Multiple Sclerosis 1998; 4: 12-15.

Luan et al. Tolerance of mice to lipopolysaccharide is correlated with inhibition of caspase-3-mediated apoptosis in mouse liver cells. Acta Biochim Biophys Sin 2007; 39(2): 96-100.

Luster et al. Endotoxin-induced cytokine gene expression and excretion in the liver. Hepatology Feb. 1994; 19(2): 480-488.

Makhija and Kingsnorth. Cytokine storm in acute pancreatitis. J Hepatobiliary Pancreat Surg 2002; 9(4):401-410.

Manning et al. Identification of L-methionine S-sulfoximine as the diastereoisomer of L-methionine SR-sulfoximine that inhibits glutamine synthetase. Biochemistry Jun. 1969; 8(6): 2681-2685.

Meister. Glutamine synthetase from mammalian tissues. Methods Enzymol 1985; 113: 185-199.

Newsholme. Why is L-glutamine metabolism important to cells of the immune system in health, postinjury, surgery or infection? J Nutr 2001; 131(9 Suppl): 2515S-2522S.

Nicklin et al. Bidirectional transport of amino acids regulates mTOR and autophagy. Cell Feb. 6, 2009; 136(3): 521-534.

Opal. Endotoxins and other sepsis triggers. Contrib. Nephrology 2010; 167: 14-24.

Park et al. Tumor necrosis factor-alpha potentiates intraneuronal Ca2+ signaling via regulation of the inositol 1,4,5-trisphosphate receptor. J Biol Chem Nov. 28, 2008; 283(48):33069-33079.

Rasola and Bernardi. The mitochondrial permeability transition pore and its involvement in cell death and in disease pathogenesis. Apoptosis 2007; 12(5): 815-833.

Rasola and Geuna. A flow cytometry assay simultaneously detects independent apoptotic parameters. Cytometry 2001; 45(2): 151-157.

Rogero et al. Dietary glutamine supplementation increases the activity of peritoneal macrophages and hemopoiesis in early-weaned mice inoculated with Mycobacterium bovis bacillus calmette-guerin. J Nutr 2008; 138(7): 1343-1348.

Ronzio et al. Studies on the mechanism of inhibition of glutamine synthetase by methionine sulfoximine. Biochemistry Mar. 1969; 8(3): 1066-1075.

Roth. Immune and cell modulation by amino acids. Clin Nutr 2007; 26(5): 535-544.

Saha et al. Gene modulation and immunoregulatory roles of interferon gamma. Cytokine 2010; 50(1): 1-14.

Schatz et al. Effect of methionine and methionine sulphoximine on rat brain S-adenosyl methionine levels. J Neurochem 1975; 24(1): 63-66.

Schwabe and Brenner. Mechanisms of liver injury. I. TNF-alpha-induced liver injury: role of IKK, JNK, and ROS pathways. Am J Physiol Gastrointest Liver Physiol 2006; 290(4): G583-G589.

Sekine et al. Liver-specific loss of beta-catenin blocks glutamine synthesis pathway activity and cytochrome P450 expression in mice. Hepatology 2006; 43(4): 817-825.

Sleyster and Knook. Relation between localization and function of rat liver Kupffer cells. Lab Invest 1982; 47(5): 484-490.

Strasser et al. Apoptosis signaling. Annu Rev Biochem 2000; 69: 217-245.

Streetz et al. Mediators of inflammation and acute phase response in the liver. Cell Mol Biol 2001; 47(4): 661-673.

Szondy et al. The effect of glutamine concentration on the activity of carbamoyl-phosphate synthase II and on the Incorporation of [3H]thymidine into DNA in rat mesenteric lymphocytes stimulated by phytohaemagglutinin. Biochem J 1989; 261(3): 979-983.

Tacke et al. Inflammatory pathways in liver homeostasis and liver injury. Clinic Rev Allerg Immunol 2009; 36(1): 4-12.

Takahashi et al. Inhibition of brain glutamine accumulation prevents cerebral edema in hyperammonemic rats. Am Physiol Soc 1991; 261: H825-H829.

Tanigami et al. Effect of glutamine synthetase inhibition on astrocyte swelling and altered astroglial protein expression during hyperammonemia in rats. Neuroscience 2005; 131(2): 437-449.

Taylor et al. Apoptosis: controlled demolition at the cellular level. Nat Rev Mol Cell Biol Mar. 2008; 9(3): 231-241.

Wang et al. Influenza virus-cytokine-protease cycle in the pathogenesis of vascular hyperpermeability in severe Influenza. J Infect Dis (Oct. 1, 2010); 202(7):991-1001.

Watanabe et al. An animal model of fulminant hepatic failure in the rat. Acta Med Okayama Dec. 1979; 33(6): 443-450.

Weitzel and Wischmeyer. Glutamine in critical illness: the time has come, the time is now. Crit Care Clin 2010; 26: 515-525.

Wu et al. Acute liver failure: mechanisms of immune-mediated liver injury. Liver International 2010; 30: 782-794.

Wullaert et al. Mechanisms of crosstalk between TNF-induced NF-kappaB and JNK activation in hepatocytes. Biochem Pharmacol 2006; 72(9): 1090-1101.

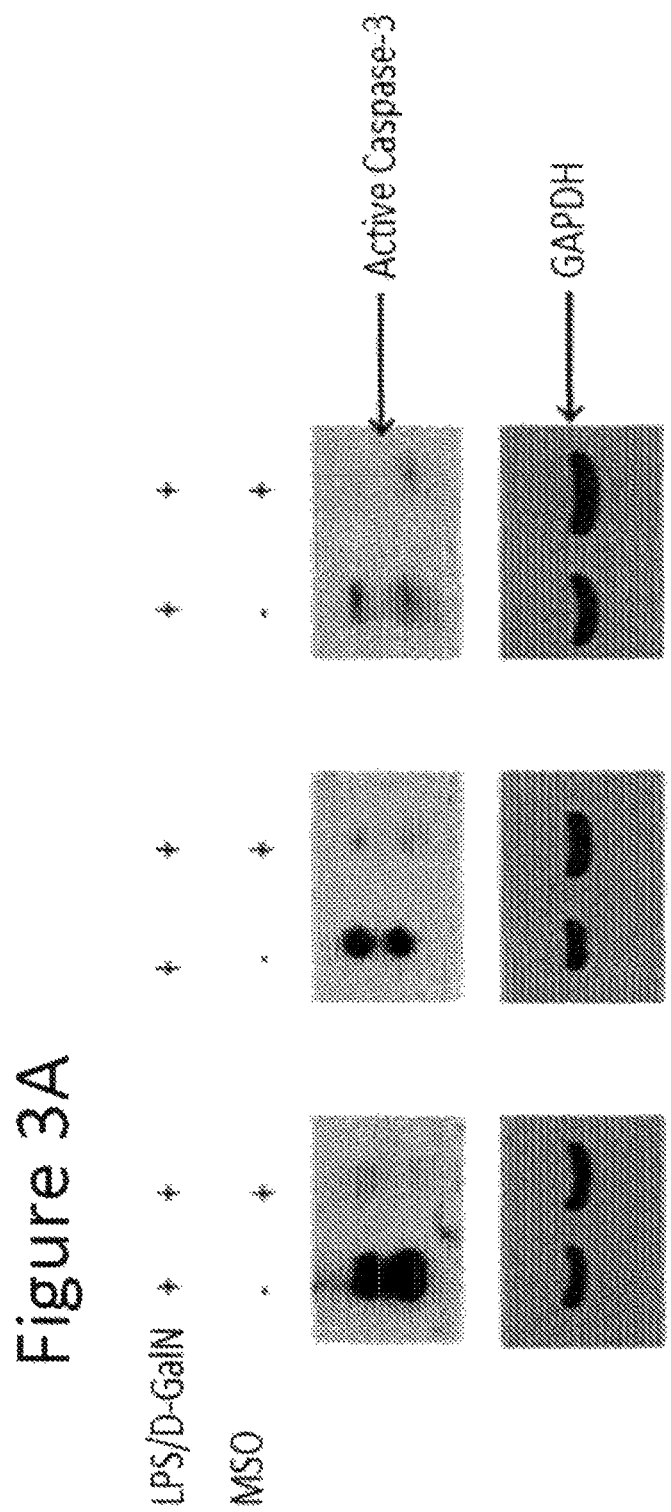

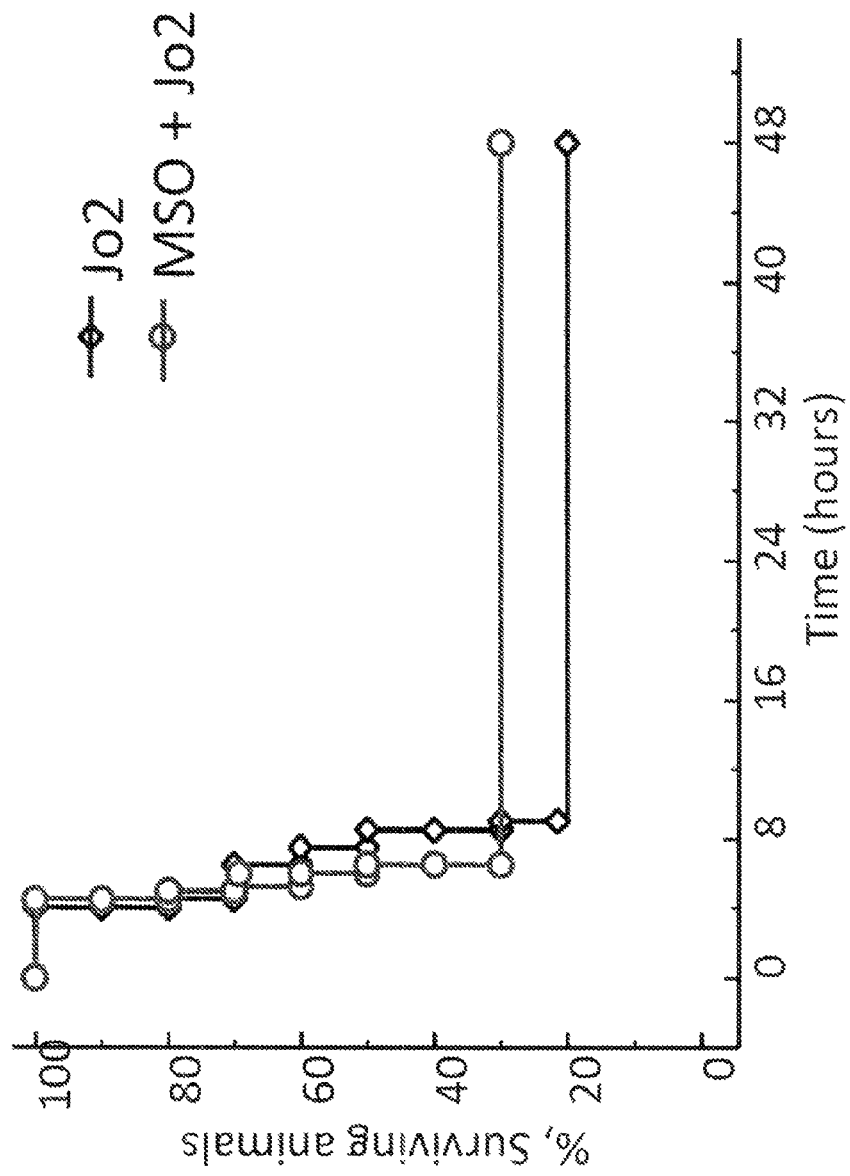

Figure 4
A - Control
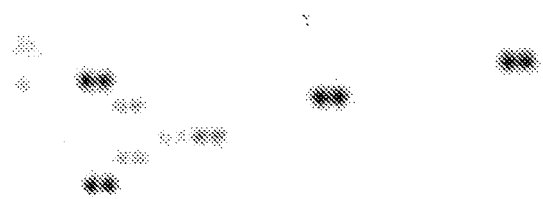
B - LPS/D-GalN
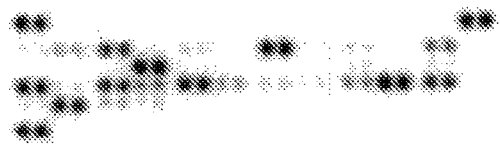
C - MSO - LPS/D-GalN
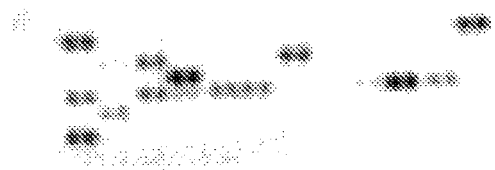

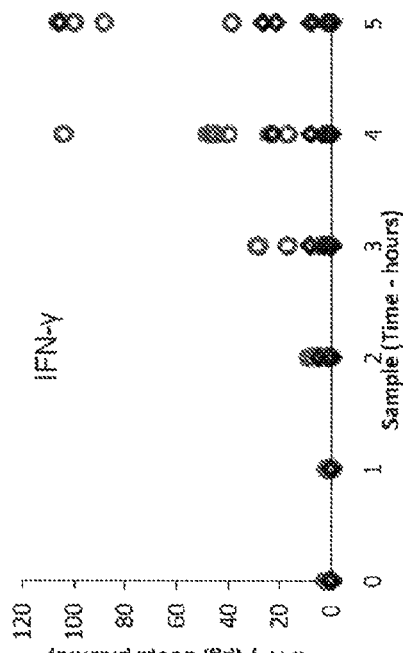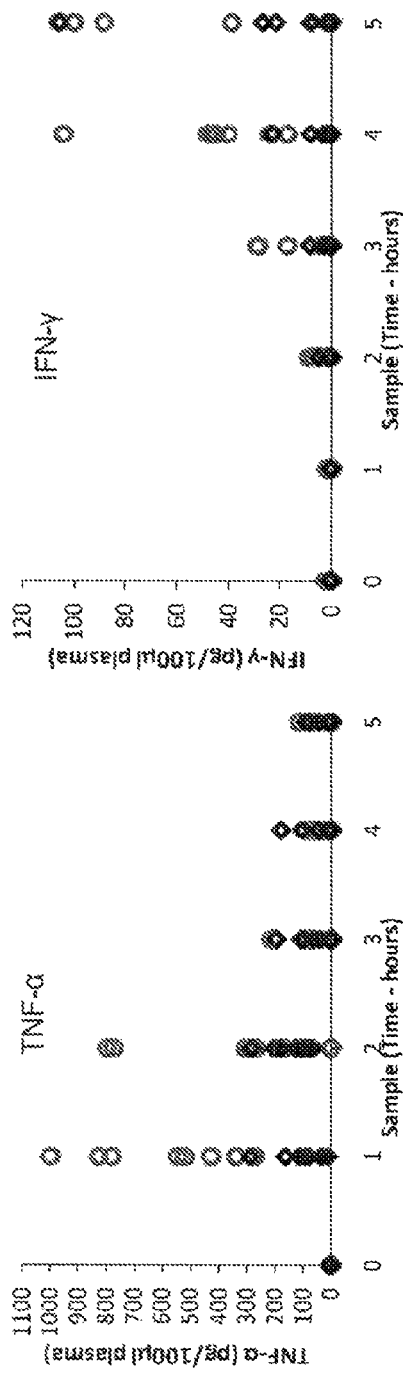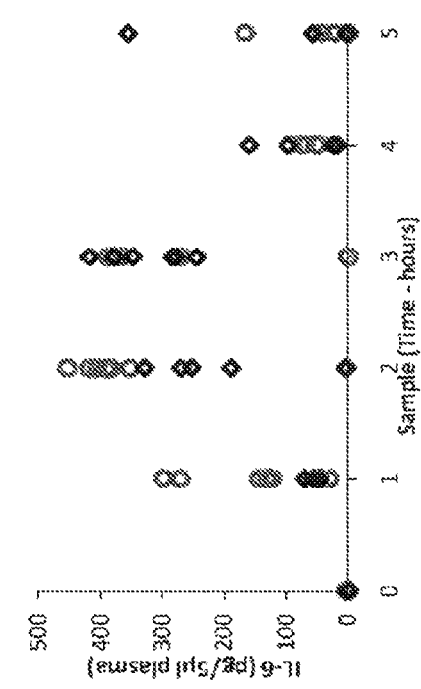

USE OF METHIONINE SULFOXIMINE TO TREAT DISEASES CAUSED BY AN INFLAMMATORY CYTOKINE RESPONSE

CROSS-REFERENCE TO RELATED APPLICATIONS

This application is a division of U.S. patent application Ser. No. 14/021,653, filed on Sep. 9, 2015, now issued U.S. Pat. No. 9,119,821, which is a continuation of U.S. patent Ser. No. 13/136,749 filed on Aug. 9, 2011, now issued U.S. Pat. No. 8,530,515, which claims the benefit of U.S. Provisional Application No. 61/371,960 filed on Aug. 9, 2010 and 61/486,810 filed on May 17, 2011. The entire disclosures of the above applications are incorporated herein by reference.

INTRODUCTION

The present technology relates to the use of L-methionine S-sulfoximine and/or L-methionine R-sulfoximine as a treatment inflammation, specifically for acute liver failure.

Sepsis and liver failure, in addition to many other diseases involving a cellular immune response, can result from the action of an inflammatory response pathway involving a variety of cytokines, one of the most important of which is TNF-α. In the case of acute liver failure, the release of these cytokines, in response to molecules such as lipopolysaccharide (LPS), viral infection, or a variety of drugs, infections, or disease states results in necrotic and apoptotic death of liver cells, leading to liver failure and death.

Acute Liver Failure (ALF) is defined as rapid deterioration of liver function in the absence of preexisting liver disease and is characterized by blood coagulation, multi-organ failure, and altered mental status. ALF can be triggered by diverse agents such as drugs (acetaminophen, thioacetamide, and α amanitin) and viruses (primarily hepatitis viruses A, B, and E). A critical feature of ALF is the mounting of a massive immune response, with recruitment of cellular effectors and uncontrolled cytokine release, a so-called cytokine storm, which destroys healthy cells and organs, leading to death. There is currently no effective therapy against ALF, a condition that kills between one and six people per million every year.

ALF is relatively rare, but it is one of many conditions resulting from an unrestrained cytokine release, and a pathological cytokine release is also believed to be involved in many other diseases that occur much more frequently, including rheumatoid arthritis, Parkinson's disease, acute pancreatitis, and complications from flu infection (e.g. sudden acute respiratory syndrome (SARS).

SUMMARY

In various aspects, the present technology includes methods and compositions for treating or preventing an inflammatory response comprising a diastereomer or diastereomeric mixture of methionine sulfoximine (MSO) diastereomers. In certain aspects, the diastereomer is L-methionine S-sulfoximine (LSMSO) or L-methionine R-sulfoximine (LRMSO). In other aspects, the composition comprises a diastereomeric mixture of LSMSO and LRMSO.

The present technology also includes a method for treating or preventing an inflammatory disorder in a human or a subject comprising administering to the subject a therapeutically effective amount of a composition comprising a diastereomer or a diastereomeric mixture of MSO. In certain aspects, the diastereomer is LSMSO or LRMSO. Such compositions may comprise a diastereomeric mixture of LSMSO and LRMSO.

In various embodiments, the inflammatory response is associated with acute liver failure, resulting (for example) from exposure of the subject to lipopolysaccharide (LPS) and/or D-galactosamine (D-GalN). The inflammatory response may also result from acute liver failure due to viral hepatitis, exposure to fluorinated hydrocarbons, trichloroethylene, ortetrachloroethane, exposure to amanita phalloides, acetaminophen, halothanes, sulfonamides, henytoins, cardiac-related hepatic ischemia renal failure, Budd-Chiari syndrome, Wilson's disease, acute fatty liver of pregnancy, amebic abscesses, or disseminated tuberculosis. In yet other aspects, inflammation is due at least in part to Parkinson's disease, inflammatory bowel disease, Alzheimer's disease, multiple sclerosis, rheumatoid arthritis, acute pancreatitis, or complications from flu infection.

Further areas of applicability will become apparent from the description provided herein. The description and specific examples in this summary are intended for purposes of illustration only and are not intended to limit the scope of the present technology.

DRAWINGS

The drawings described herein are for illustrative purposes only of selected embodiments and not all possible implementations, and are not intended to limit the scope of the present disclosure.

Figure 2:
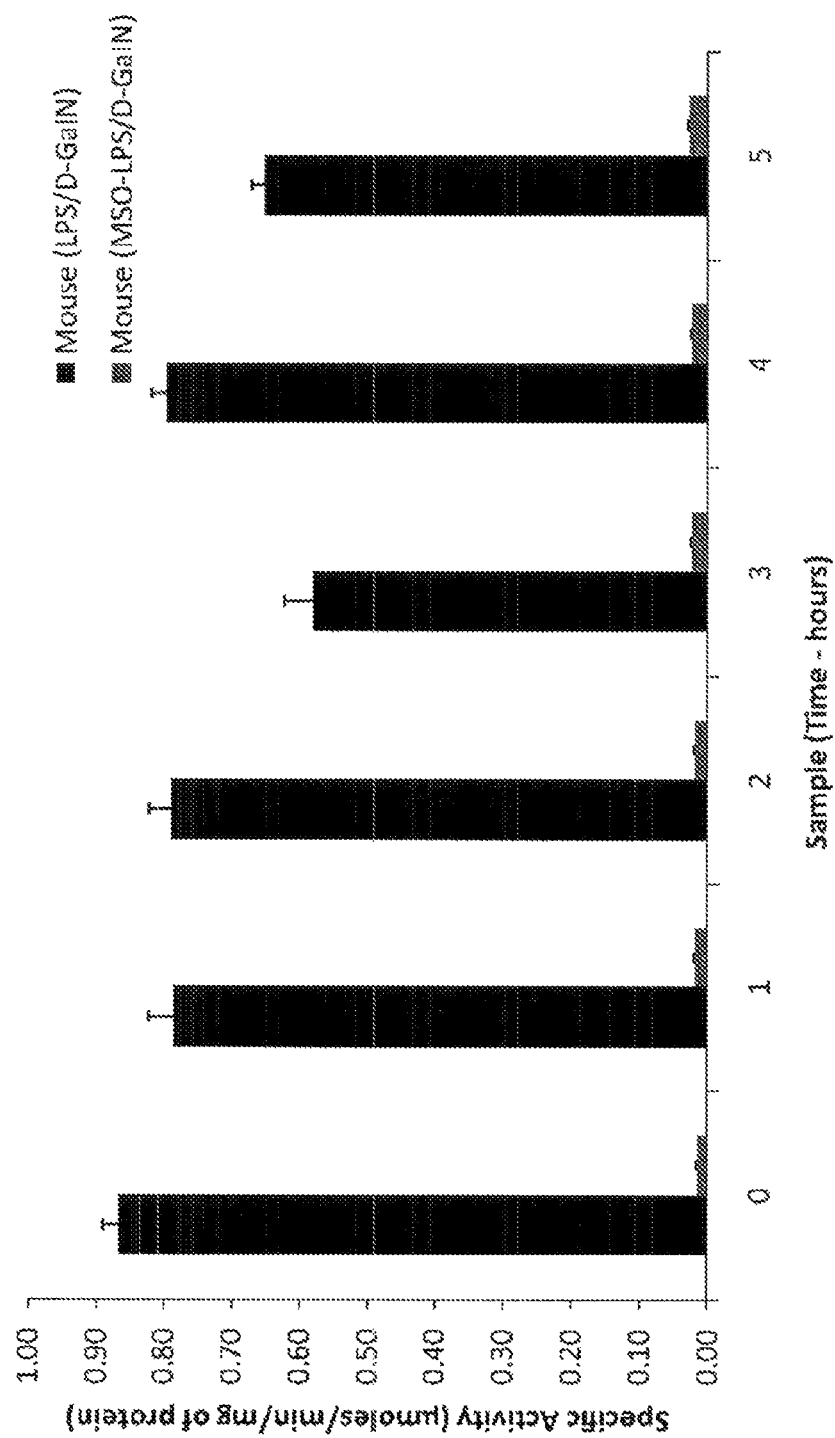
Figure 3C:
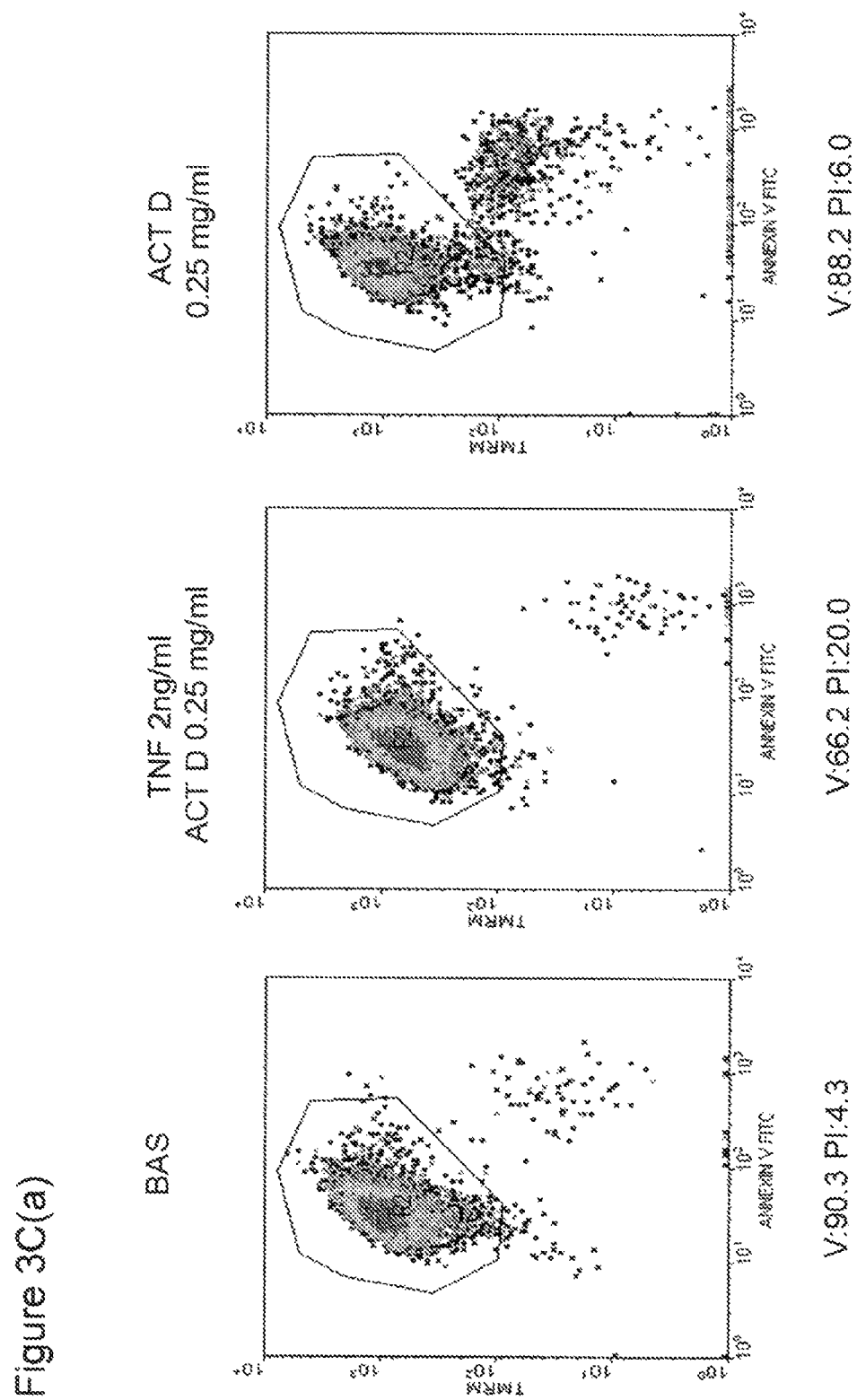
Figure 3C:
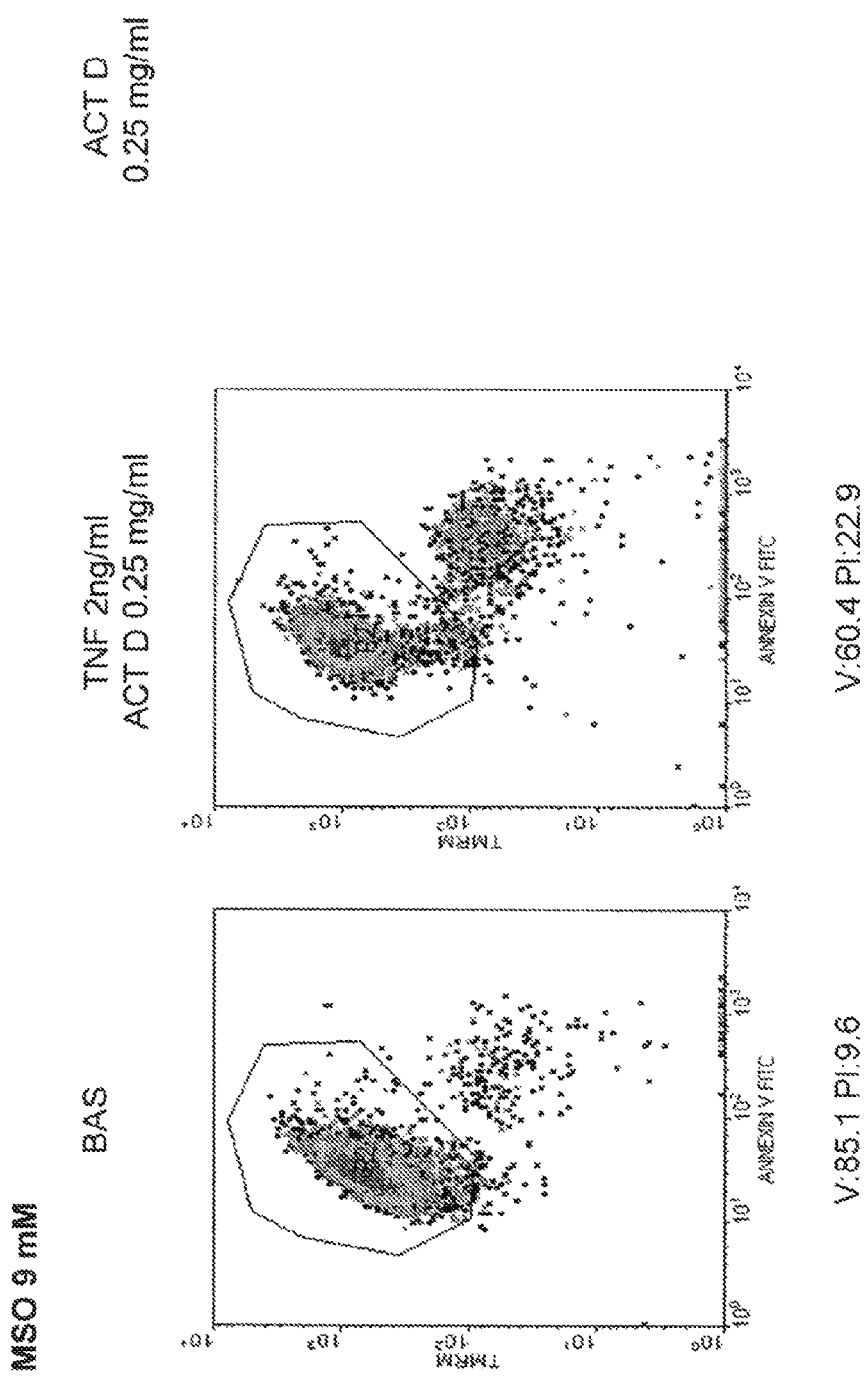
Figure 3C:
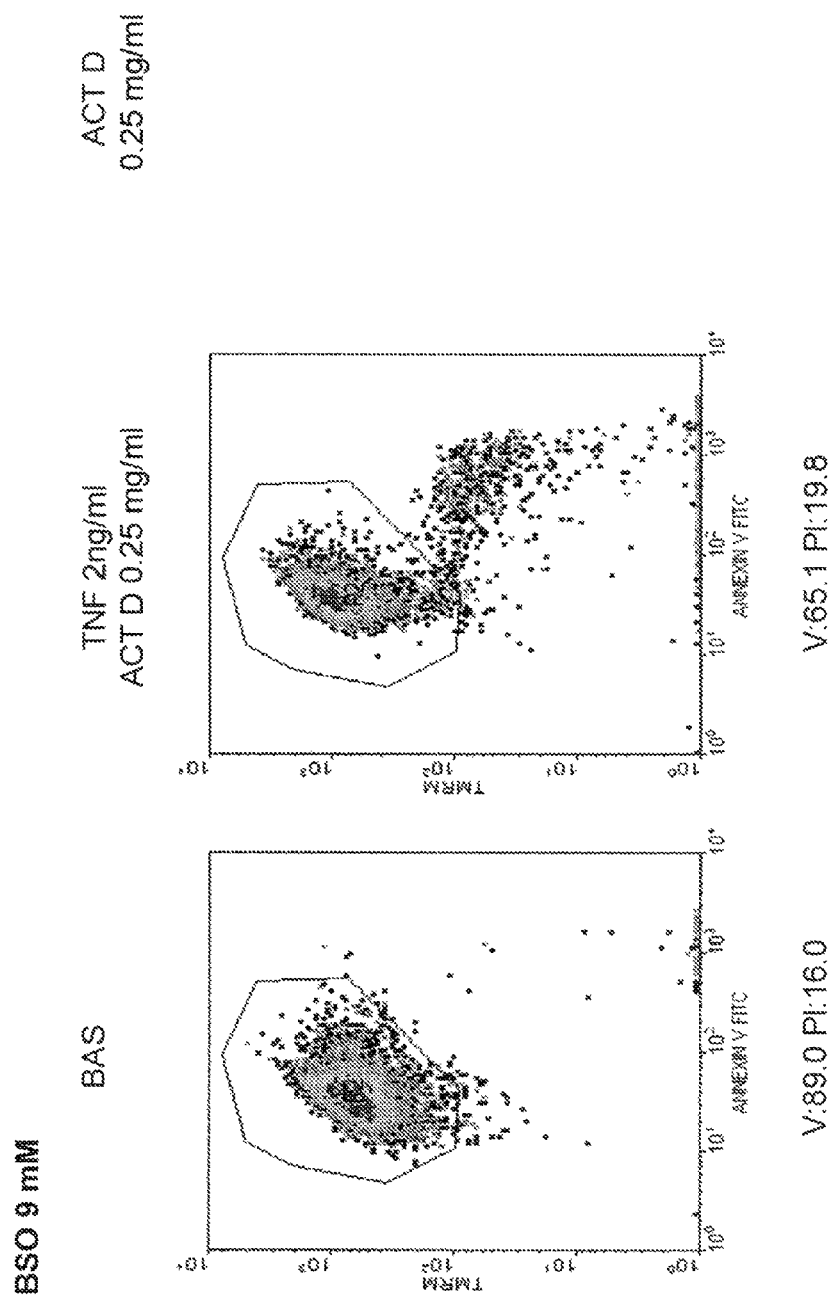

FIG. 1 illustrates the survival of male and female CD1 mice pretreated with either MSO (open circles) (50 mg/kg IP) or saline (open diamonds) three hours prior to injection with LPS and D-galactosamine (D-GalN) at time zero to induce liver failure. Time of death is recorded as hours after LPS/D-GalN injection (X axis), and percent of remaining animals are plotted on the Y axis. For males (left), 4 out of 21 mice injected with LPS/D-GalN survived. Two tailed p values for these two groups <0.002. For females (right), 3 out of 14 mice injected with LPS/D-GalN survived. Two tailed p values for these two groups <0.005;

FIG. 2 illustrates glutamine synthetase activities measured in liver extracts from mice treated with LPS and D-GalN three hours after IP injection of either saline (black bars) or MSO (grey bars). Each time point represents the average glutamine synthetase activity in liver extracts from 15 animals;

FIG. 3A, FIG. 3B, and FIG. 3C illustrate the effect of MSO treatment on extrinsic apoptosis induction. FIG. 3A illustrates caspase-3 activation. Western immunoblots of liver extracts are hybridized with anti-cleaved, i.e. activated caspase-3. Three different experiments are shown. Each experiment consists of a liver from two LPS/D-GalN-treated mice—one pretreated with saline and one pretreated with MSO, as shown above each blot. Blots are probed with anti-GAPDH as a loading control. FIG. 3B illustrates survival of CD1 mice pretreated with either MSO (50 mg/kg I.P.) or saline three hours prior to injection with the anti-Fas Jo2 agonist antibody. Time of death is recorded as hours after LPS/D-GalN injection (X axis), and percent of remaining animals is plotted on the Y axis. FIG. 3C illustrates the effect of MSO and BSO on apoptosis induced by TNF-α. Output of multiparametric FACS analyses. Mouse liver progenitor cells, MLP 29, are incubated for one hour with either no addition (first lane, FIG. 3C(a)), 9 mM MSO (second lane, FIG. 3C(b)), or 9 mM BSO (third lane, FIG. 3C(c)), then exposed for 10 hours to either no addition—

Figure 5A:
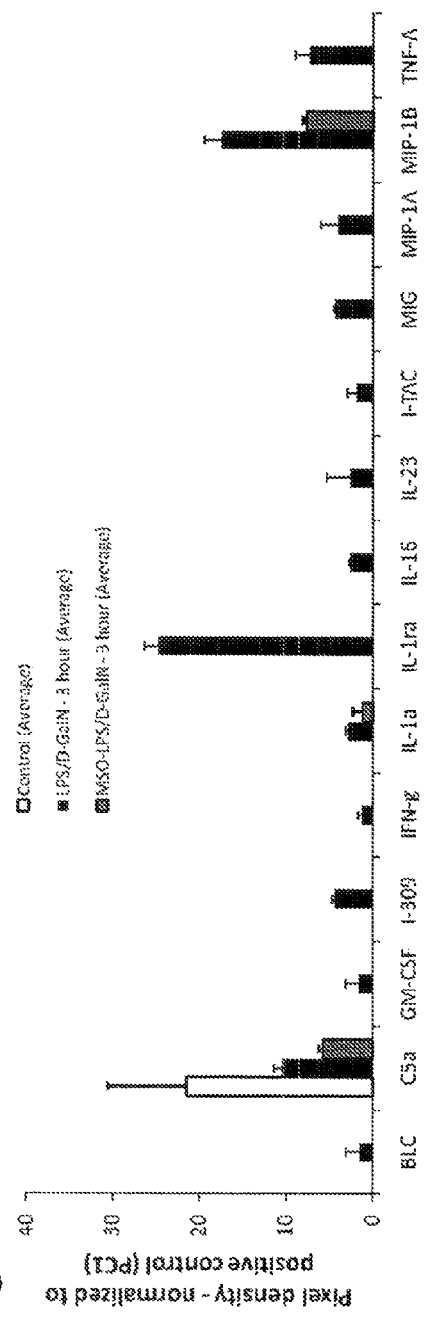
Figure 5B:
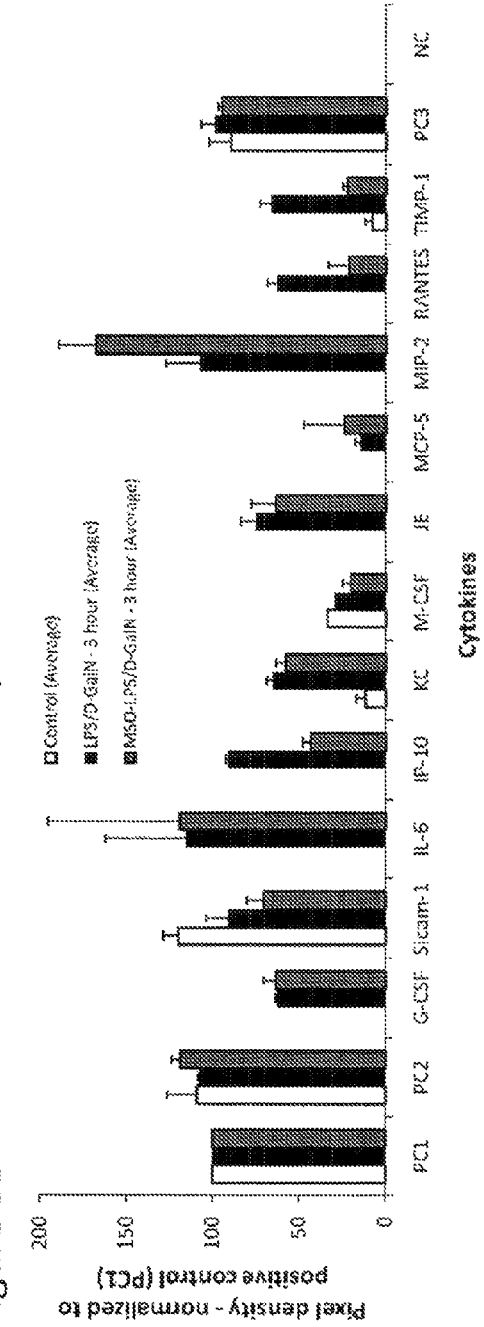
Figure 7:
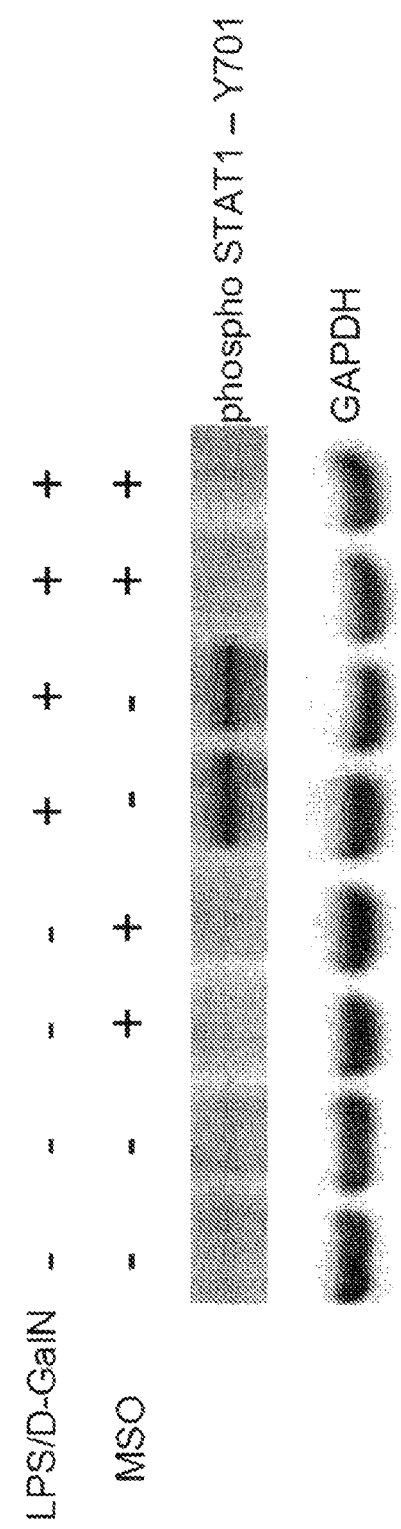

(BAS, first column), TNF-α plus actinomycin D (second column), or actinomycin D alone (third column). Viable cells (V) are delimited by the quadrant. Apoptotic cells display mitochondrial depolarization (reduced TMRM staining) and/or expose phosphatidylserine on their surface (increased Annexin V-FITC staining). Propidium iodide-positive, i.e. dead cells (PI), are evaluated on a PI vs TMRM diagram (not shown); these cells are excluded from the reported plots, but the percentage of propidium iodide positive (i.e. dead) cells is shown in each box (PI), as is the percentage of viable cells (V);

FIG. 4 illustrates nitrocellulose membrane-based cytokine arrays. Panel A shows cytokines in plasma from a mouse not treated with either MSO or LPS-D-GalN. Panel B shows cytokines in plasma from a mouse mice treated with LPS/D-GalN for three hours. Panel C shows cytokines in plasma from a mouse pretreated with MSO three hours before being treated with LPS/D-GalN for three hours;

FIG. 5A and FIG. 5B illustrate changes in cytokines calculated from cytokine array blots. Each treatment group has two animals (two blots, one for each animal) in it and the values for 25 different cytokines detected were averaged for each group and represented as pixel densities, normalized to the average pixel densities of the positive controls (PC1), and plotted on this bar graph. These figures show average cytokine intensities in control, LPS/D-GalN and MSO-LPS/D-GalN treated animals. Cytokines are arbitrarily grouped into those with a low signal (FIG. 5A) and those with a high signal (FIG. 5B) to better observe the effects of MSO treatment on cytokine production. The cytokines not detected on the blots are not shown. Open bars represent the cytokine values for untreated negative control mice. Black bars represent the cytokine values for mice treated with LPS/D-GalN. Grey bars represent the cytokine values for mice pretreated with MSO three hours before being injected with LPS/D-GalN. The higher of the two averaged values for each cytokine is indicated by the line extending above each bar;

FIG. 6A, FIG. 6B, and FIG. 6C illustrate ELISA quantitation cytokine levels in plasma from LPS/D-GalN treated mice. The time zero values show the levels of each cytokine in negative control mice, not treated with LPS/D-GalN but injected with either saline (n=7) or MSO (n=7) three hours prior to be killed. Each of the hour time points shows cytokine levels in 7 or 8 mice killed at that time point after LPS/D-GalN treatment. For each cytokine, open circles represent cytokine levels in plasma isolated from mice pretreated with saline, and open diamonds represent cytokine levels in plasma isolated from mice pretreated with MSO prior to LPS/D-GalN treatment. FIG. 6A illustrates TNF-α levels. FIG. 6B illustrates IFN-γ levels. FIG. 6C illustrates IL-6 levels; and FIG. 7 illustrates immunoblots of liver tissue homogenates from LPS/D-GalN treated mice probed with anti phospho-STAT1. The top two lines show treatments, either LPS/D-GalN, MSO, neither, or both. The blot shows that LPS/D-GalN treatment phosphorylates and activates STAT1, but not if mice are pretreated with MSO. Glyceraldehyde phosphate dehydrogenase (GAPDH) is shown as a loading control.

Corresponding reference numerals indicate corresponding parts throughout the several views of the drawings.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

In various embodiments, the present technology is based on the unanticipated finding of use of the methionine sulfoximine (MSO) and its diastereomeric isomers L-methionine S-sulfoximine and/or L-methionine R-sulfoximine to treat or prevent inflammation that results in acute liver failure or other inflammatory response diseases.

The inflammation that results from an aberrant immune response that produces toxic levels of inflammatory cytokines such as TNF-α. Part of the mammalian immune response is cellular immunity. Macrophages and other cells involved in the immune response recognize and respond to foreign molecules by releasing cytokines, producing responses in different cell types that neutralize and eliminate the infection.

Although cellular immunity acts to protect the host from infection, there are many disease states that involve an aberrant immune response that destroys the host's own cells. Cytokines can signal immune cells such as T-cells and macrophages to both travel to the site of infection and produce more cytokines. But a feedback loop can occur in this response resulting in overstimulation of these cells, overproduction of cytokines, and the death of healthy cells as well as foreign invaders and infected cells. It is not understood how this response can go out of control, but when it does, the medical consequences can be grave. In the case of acute liver failure (ALF), the release of TNF-α and other cytokines in response to bacterial infection (e.g., in toxic shock), viral infection (e.g., in hepatitis), or specific chemicals (e.g., acetaminophen (Tylenol™) poisoning or thioacetamide poisoning), can lead to this "cytokine storm," activating cellular death pathways in an uncontrolled fashion that ultimately destroys the host's own liver cells and leads to liver failure and death.

In various aspects, the present technology provides a composition for treating or preventing an inflammatory response in a human or subject comprising a diastereomer or diastereomeric mixture of MSO. In certain aspects, the diastereomer or diastereomeric mixture (generally referred to herein as "MSO") is selected from the group consisting of L-methionine S-sulfoximine (LSMSO), L-methionine R-sulfoximine (LRMSO), and mixtures thereof (including diastereomeric mixtures). Compounds, compositions and methodologies among those useful herein are disclosed in U.S. Pat. No. 6,875,792, Brusilow et al., issued Apr. 5, 2005.

LSMSO is represented as follows:

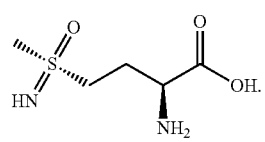

LRMSO is represented as follows:

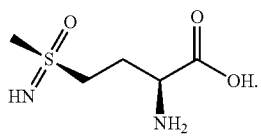

Methionine sulfoximine (MSO) is a modified amino acid that acts as a very strong mechanism-based inhibitor of glutamine synthetase, the ATP-dependent enzyme that converts glutamate and $NH_3$ into glutamine—a central reaction in cellular nitrogen metabolism, a selective inhibitor of gamma-glutamylcysteine synthetase. Glutamine/glutamate metabolism is complicated, and the in vivo inflammatory response involves a complex and not-well-defined set of reactions, making it difficult to draw a "straight line" from glutamine or glutamine synthetase directly to cytokine release/cytokine storm. Additionally, MSO also inhibits other targets. It is an inhibitor of the first step of glutathione synthesis—γ glutamyl cysteine synthetase, and thus can affect glutathione levels. MSO can also inhibit the synthesis of S-adenosyl methionine (SAM).

In certain aspects, the inflammatory response results in ALF. (As used herein "result" refers to direct or indirect causation or mediation, in which may be sole or in combination with other agents or conditions.) Common causes for ALF include viral hepatitis, exposure to certain drugs and toxins (e.g., fluorinated hydrocarbons (e.g., trichloroethylene and tetrachloroethane), amanita phalloides (e.g., commonly found in the "death-cap mushroom"), acetaminophen (paracetamol), halothanes, sulfonamides, henytoins), cardiac-related hepatic ischemia (e.g., myocardial infarction, cardiac arrest, cardiomyopathy, and pulmonary embolism), renal failure, occlusion of hepatic venous outflow (e.g., Budd-Chiari syndrome), Wilson's disease, acute fatty liver of pregnancy, amebic abscesses, and disseminated tuberculosis.

In other aspects, the ALF results from exposure of the subject to lipopolysaccharide and/or D-galactosamine. ALF can be induced in the subject through lipopolysaccharide (LPS) and D-galactosamine (D-GalN), which induces an inflammatory response involving TNF-α production and a hepatocyte-specific transcriptional block. This induces a systemic response which is predominantly directed towards the liver. As the liver fails, the resultant hyperammonemia produces brain edema similar to the brain swelling seen in hepatic encephalopathy of humans that results from liver disease. In certain aspects, brain swelling is prevented in hyperammonemic rats by treatment with LSMSO.

Under these conditions, binding of TNF-α to its cognate receptor on hepatocytes eventually leads to their apoptosis. MSO appears to protect a subject from liver failure induced by LPS and D-GalN, and further MSO treatment appears to protect the subject by inhibiting the release of cytokines (i.e. the "cytokine storm") responsible for the activation of cell death pathways that lead to liver cell death, liver failure, and ultimately death of the subject. The mechanism therefore appears to involve either some undiscovered link between glutamine synthetase and early cytokine release, or MSO has a previously uncharacterized target that mediates cellular immunity. In either case, the use of MSO to treat acute liver failure or other diseases involving a "cytokine storm" resulting from an aberrant immune response is a novel and unexpected use for this compound.

Treatment with MSO (i) increases the subject survival; (ii) reduces glutamine synthetase activity, without inhibiting its other target, γ-glutamyl cysteine synthetase; (iii) inhibits death receptor-mediated apoptosis in hepatocytes upstream to cytokine binding; (iv) reduces the overall inflammatory cytokine response, including a significant decrease in TNF-α induction in vivo and ex vivo, and in interferon-γ level and signaling. MSO appears to target the early steps of the cytokine response to LPS and D-GalN, suggesting that the pharmacological inhibition of glutamine synthetase may be exploited to treat inflammation.

In other aspects, MSO is used to treat other diseases for which an inflammatory immune response is believed to be clinically relevant to the disease process. These diseases include, but are not limited to, Parkinson's disease, inflammatory bowel disease, Alzheimer's disease, multiple sclerosis, rheumatoid arthritis, acute pancreatitis, and complications from flu infection (e.g., severe acute respiratory syndrome (SARS)).

The present technology provides methods for treating or preventing inflammation in a human or a subject comprising administering to the subject a therapeutically effective amount of a composition comprising MSO, e.g., a diastereomer or a diastereomeric mixture of MSO.

The methods and compositions of the present technology comprise the administration of, and compositions having dosage levels suitable for administration of, a safe and effective amount of LSMSO, LRMSO or mixtures thereof. A "safe and effective" amount of MSO is an amount that is sufficient to have the desired therapeutic effect in the human or lower animal subject, without undue adverse side effects (such as toxicity, irritation, or allergic response), commensurate with a reasonable benefit/risk ratio when used in the manner of this technology. The specific safe and effective amount of MSO will, obviously, vary with such factors as the particular condition being treated, the physical condition of the patient, the nature of concurrent therapy (if any), the specific MSO compound used, the specific route of administration and dosage form, the carrier employed, and the desired dosage regimen. For example, in various embodiments MSO may be administered to a subject in low doses of less than or about 20 mg/kg, of less than or about 18 mg/kg, of less than or about 15 mg/kg, of less than or about 10 mg/kg, less than or about 8 mg/kg, less than or about 5 mg/kg, or less than or about 2.5 mg/kg. Methods and associated compositions may comprise administration of a substantially pure diastereomer, i.e., LSMSO with essentially no LRMSO, or LRMSO with essentially no LSMSO. In some embodiments, methods and compositions may comprise mixtures of diastereomers, such as diastereomeric mixtures. (A "diastereomeric mixture" comprises equal parts of individual diastereomers.) The duration of the treatment time with MSO is not particularly limited but can be administered in a single dose in instances of ALF or weekly, biweekly, or monthly for a chronic disease associated with liver failure.

The biological and pharmacological activity of a compound may be sensitive to the stereochemistry of the compound. For example, diastereomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one diastereomer may be more active or may exhibit beneficial effects when enriched relative to the other diastereomer or when separated from the other diastereomer.

Additionally, one skilled in the art would know how to separate, enrich, or selectively prepare the diastereomers of the compounds of this technology.

The present technology provides compositions comprising a safe and effective amount of MSO and a pharmaceutically acceptable carrier. As used herein, such a "pharmaceutically acceptable" carrier is one that is suitable for use with humans and/or animals without undue adverse side effects (such as toxicity, irritation, and allergic response) commensurate with a reasonable benefit/risk ratio. MSO thereof may be administered to the subject orally, intravenously, subcutaneously, or transdermally. For example, an intravenous formulation can be administered as a sterile buffered saline solution, while an oral preparation can be prepared with the standard pharmaceutically acceptable excipients through standard pharmaceutical manufacturing techniques.

In various embodiments, the pharmaceutical carrier is a solid or liquid. Solid form preparations include powders, tablets, dispersible granules, capsules, and cachets.

A solid carrier can be one or more substances which can also act as diluents, flavoring agents, solubilizers, lubricants, suspending agents, binders, or tablet disintegrating agents; it can also be an encapsulating material. In powders, the carrier is generally a finely divided solid which is in a mixture with the finely divided active component. In tablets, the active compound is mixed with the carrier having the necessary binding properties in suitable proportions and compacted in the shape and size desired. Powders and tablets may contain from about 5% to about 70% by weight of the active ingredient. Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter and the like.

Pharmaceutical compositions can include the formulation of the active compound with encapsulating material as a carrier providing a capsule in which the active component (with or without other carriers) is surrounded by a carrier, which is thus in association with it. In a similar manner, cachets are also included. Tablets, powders, cachets, and capsules can be used as solid dosage forms suitable for oral administration.

Liquid pharmaceutical compositions include solutions suitable for oral or parenteral administration, or suspensions, and emulsions suitable for oral administration. Parenteral compositions may comprise sterile solutions of the active component in a pharmaceutically-acceptable solvent such as water, ethanol, propylene glycol or mixtures thereof. Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water or other appropriate solvents and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Compositions and methods of the present technology are illustrated by the following non-limiting example.

EXAMPLE

In the following example, the therapeutic use of MSO in a LPS/D-GalN mouse model of ALF is studied to evaluate if MSO affects the early events that lead to liver failure. In this example, pretreatment with MSO greatly increases the survival of mice challenged with LPS/D-GalN. The mechanism of action of MSO in this system appears to involve a reduction in the early cytokine response of macrophages, indicating that glutamine synthetase activity may be required for cytokine synthesis elicited by LPS/D-GalN in inflammatory cells.

Materials and Methods

Six to eight week old CD1 mice are obtained from Charles River. Animals were housed in Wayne State University or University of Padova, Vallisneri Interdepartmental Complex animal quarters until the time of the experiment. Food was withdrawn the night before the day of the experiment. All experiments were approved by the Animal Investigation Committee of Wayne State University or by the Authority of the University of Padova and authorized by the Italian Ministry of Health. Both universities comply with the criteria outlined in the "Guide for the Care and Use of Laboratory Animals" prepared by the National Academy of Sciences and published by the National Institutes of Health (NIH publication 86-23 revised 1985).

Animals were divided into two groups. Group one animals consisted of both male and female mice injected with LPS and D-GalN to induce hepatic failure. Survival was monitored post LPS/D-GalN administration and the time of injection was considered to be zero hour (t=0). Group two animals consisted of mice injected with MSO three hours prior to LPS and D-GalN administration. A mixture of LPS (20 µg/kg body weight, sigma—LPS from $E.\ coli$ 0111:B4 Sigma #L2630) and D-GalN (800 mg/kg body weight, Sigma #G1639) was prepared in saline and administered intraperitoneally (IP). MSO (50 mg/kg body weight, Sigma #M5379) was also prepared in saline and administered IP. For analysis of the effect of MSO treatment on the cell death pathway activated by the Fas ligand, mice were pre-treated with MSO as described above, and at time zero were injected with Jo2 antibody (200 m/kg).

Animals were monitored continuously post LPS/D-GalN or Jo2 administration. Six to ten hours after treatment with LPS/D-GalN animals became very sick, and they were euthanized if their distress increased to the extent that they had difficulty moving, or if they were unresponsive to prodding. The time of death was recorded as hours after LPS/D-GalN injection. Fisher's exact test was used to determine two-tailed p values for the statistical between the treated and untreated groups.

Immunoblots of cleaved caspase-3 and phospho-STAT proteins: Liver homogenates were prepared from male mice five hours after IP administration of LPS/D-GalN. The proteins in liver homogenates were separated by SDS-PAGE in 12% acrylamide-0.8% bisacrylamide slab mini gels, electro-blotted onto nitrocellulose membranes (Amersham Biosciences Little Chalfont, UK—Hybond™-ECL™) and the membranes were sequentially immunoblotted with antibodies against cleaved caspase-3. Glyceraldehyde-3-phosphate dehydrogenase (GAPDH—Chemicon, Milano, Italy) was used as a loading control). Other antibodies used in these studies included Phospho-STAT antibodies (cell Signaling cat #9914), including phospho-STAT1 (Tyr701), phospho- STAT2 (Tyr690), phospho-STAT3 (Tyr705), phospho-STAT3 (Ser727), phospho-STAT5 (Tyr694), and phospho-STAT6 (Tyr641). Antirabbit IgG, HRP-linked secondary antibody was used and the blots were developed either using the Immun-Star WesternC Kit (BIO-RAD cat #170-5070) on a BIO-RAD imager, or using an ECL system (Amersham Biosciences).

Flow cytometry recordings of apoptotic changes were performed as described (Gramaglia et al. Apoptosis to necrosis switching downstream of apoptosome formation requires inhibition of both glycolysis and oxidative phosphorylation in a BCL-X(L)- and PKB/AKT-independent fashion. (Cell Death Differ 2004; 11(3): 342-53; and Rasola et al. A flow cytometry assay simultaneously detects independent apoptotic parameters. Cytometry 2001; 45(2): 151-7). After induction of apoptosis, MLP 29 cells were resuspended in 135 mM NaCl, 10 mM Hepes, 5 mM $CaCl_2$ and incubated for 15 min at 37° C. in FITC-conjugated Annexin-V, TMRM (200 nM) and propidium iodide (PI, 1 μg/ml) to detect mitochondrial depolarization (reduced TMRM staining), phosphatidylserine exposure on the cell surface (increased FITC-conjugated Annexin-V staining), and loss of plasma membrane integrity (PI permeability and staining). Samples were analyzed on a FACSCalibur flow cytometer (Becton Dickinson, San Diego, Calif.). Data acquisition was performed using CellQuest software and data analysis with WinMD1 software. Each experiment was repeated at least four times.

Peritoneal macrophages were isolated from the abdomens of CD-1 mice, and $2 \times 10^4$ cells were added to each well of a 6-well cell culture plate. The cells were incubated in RPMI—1640 (with 2.05 mM glutamine) with 5% fetal calf serum and 1% penicillin/streptomycin (all solutions were from Hyclone) for 4 hours. The medium was then changed to remove any non-adherent cells, and the cells were again incubated in a 5% $CO_2$ incubator for 16 hours. In each plate, one well was a negative control (no treatment), one well was a MSO control (9 mM) and one well was a LPS control (1 μg/ml LPS). The other three wells were treated with 9 mM MSO and 1 μg/ml LPS. One well was treated with MSO for 3 hours, and LPS was then added. In another well, LPS and MSO were added at the same time. Time of LPS addition was considered time zero. Four hours after LPS addition the cell culture medium was collected and 50 μL of the medium was mixed with 50 μl of blocking buffer and used for the TNF-α ELISA assay.

Tissue and plasma were collected from male mice, which were divided into two groups. One group was injected with saline three hours prior to LPS/D-GalN injections. The second group was given MSO three hours prior to being injected with LPS/D-GalN. Control mice (t=0) were treated with MSO or saline for 3 hours and then euthanized (not exposed to LPS/D-GalN). After LPS/D-GalN injection at time zero, tissue and plasma samples were collected at one-hour time intervals from 1 to 5 hours.

For experiments analyzing plasma cytokines, the male mice from the groups described above were anesthetized using Avertin (solution of 15.5 mls of tert-amyl alcohol—Sigma #240486 and 25 g of 2-2-2 tribromoethanol—Sigma #T48402) and blood was collected by cardiac puncture. Plasma was obtained by transferring blood to plasma separator tubes containing lithium heparin (BD Microtainer tubes). Plasma samples were immediately frozen on dry ice and stored at −80° C.

To analyze enzyme activities liver homogenates were prepared from liver tissue excised and immediately homogenized in ice-cold buffer consisting of 250 mM sucrose, 10 mM Tris and 0.1 mM EGTA with protease inhibitor cocktail (Sigma #P8340). The homogenized tissue was centrifuged at 2375×g for 5 min. The tissue supernatant fraction was frozen on dry ice and stored at −80° C.

Glutamine synthetase was assayed as described by Meister, A. Glutamine synthetase from mammalian tissues. Methods Enzymol 1985; 113: 185-99. Liver supernatant (100 μg) was incubated in buffer (0.1 M imidazole, 100 mM L-glutamine, 0.2 mM $MnCl_2$, 62.5 mM hydroxylamine, 10 mM sodium arsenate and 0.4 mM ADP) at 37° C. for 15 min. The reaction with the substrates glutamine and hydroxylamine was stopped using ferric chloride stop solution (0.37 M $FeCl_3$, 0.67 M HCl, 0.20 M TCA) and the colorimetric product formed—γ-glutamyl hydroxamate—was measured at 535 nm. The absorbance values were converted to activities by comparison to a standard curve of pure glutamyl hydroxamate (a generous gift from Arthur J. Cooper, Department of Biochemistry and Molecular Biology, New York Medical College). Graphpad analysis software was used to obtain two-tailed p values using an unpaired t test. γ-glutamyl cysteine synthetase was assayed in the same extracts as described by Griffith et al. Selective inhibition of gamma-glutamyl-cycle enzymes by substrate analogs. Proc Natl Acad Sci USA 1977; 74(8): 3330-4.

Mouse cytokine array kits (Proteome Profiler Arrays—cat # ARY006) were obtained from R&D Systems and used according to the manufacturer's guidelines. Each array, which consisted of a nitrocellulose membrane spotted with 40 different mouse cytokines, was tested with two hundred microliters of plasma from one animal. Each condition was duplicated—two mice for each group. Control blots were from plasma collected from two untreated mice (not injected with LPS/D-GalN and/or MSO). For untreated and MSO-treated groups, plasma was collected at either 1 hour or 3 hours after LPS/D-GalN administration. The blots were developed using the Immun-Star WesternC Kit (BIO-RAD cat #170-5070) on a BIO-RAD imager. The corresponding Quantity One software of the BIO-RAD imager was used to quantify the signal obtained on the blots.

TNF-α, IFN-γ, and IL-6 ELISA kits were obtained from eBioscience, and experiments were performed using the manufacturer's guidelines for 96-well plate experiments. One hundred microliters of plasma was used per well. The TNF-α ELISA assay had a sensitivity of 8-1000 pg/ml and the IFN-γ ELISA had a sensitivity of 0.75-100 pg/ml. The IL-6 ELISA assay had a sensitivity of 0-500 pg/ml, and the combination of ELISA sensitivity and the amounts of IL6 in plasma required us to reduce the amount of plasma tested to 5 μL.

Results

Based on the above testing, MSO prevents LPS/D-GalN induced ALF lethality in mice: FIG. 1 shows survival curves for CD1 mice treated with LPS/D-GalN to induce liver failure. Mice were injected with MSO three hours prior to LPS/D-GalN treatment. Without MSO pretreatment, LPS/D-GalN administration resulted in death 6-10 hours after administration. MSO pretreatment increased male survival from 19% to 71% (FIG. 1A) n=21; p<0.002. MSO pretreatment increased female survival from 27% to 81% (FIG. 1B) n=14; p<0.005. MSO therefore substantially increases survival in both male and female mice with LPS/D-GalN induced ALF.

MSO treatment reduces activity of glutamine synthetase but not gamma-glutamylcysteine synthetase: MSO is a well-characterized inhibitor of glutamine synthetase and of the enzyme catalyzing the first step of glutathione synthesis, γ-glutamylcysteine synthetase (GGCS). Glutamine synthetase activity was assayed in liver extracts from LPS/D-GalN treated animals. FIG. 2 shows that at all time points, MSO pre-treatment reduced glutamine synthetase activity to less than 10% of that found in animals pre-treated with saline, supporting the conclusion that inhibition of glutamine synthetase activity might be involved in the therapeutic effects of this drug.

Liver extracts from LPS/D-GalN treated mice were also assayed for GGCS activity and found that extracts from mice pre-treated with 50 mg/kg MSO had the same GGCS activities as extracts from mice pre-treated with saline, so this dose of MSO does not affect GGCS (data not shown).

To further test the possibility that the decrease in cellular immunity might be due to GGCS inhibition, the effects of the GGCS inhibitor buthionine sulfoximine (BSO) on survival of LPS/D-GalN treated animals was tested even though a previous study had shown that inhibition of GGCS activity by BSO actually augments the inflammatory process initiated by LPS treatment (Haddad, J. J. L-Buthionine-(S, R)-sulfoximine, an irreversible inhibitor of gammaglutamylcysteine synthetase, augments LPS-mediated pro-inflammatory cytokine biosynthesis: evidence for the implication of an IkappaB-alpha/NF-kappaB insensitive pathway. Eur Cytokine Netw 2001; 12(4): 614-24). IP injections of 800 mg/kg BSO (Drew et al. The effects of buthionine sulphoximine (BSO) on glutathione depletion and xenobiotic biotransformation. Biochem Pharmacol 1984; 33(19):2989-94) were administered 3 hours prior to LPS/D-GalN and mouse survival was monitored. BSO is known to inhibit GGCS 100 times more effectively than MSO. However, BSO pretreatment had no effect on either glutamine synthetase activities or on survival of mice treated with LPS/D-GalN. Only 3 out of 20 treated mice survived (15% survival). The increased survival and reduced immune response seen in the effects of MSO on the LPS/D-GalN induced ALF mouse model cannot therefore be accounted for by its action on γ-glutamyl cysteine synthesis.

LPS/D-GalN treatment prompts ALF and death as LPS induces a sudden and dramatic rise in macrophage TNF-α synthesis, and TNF-α in turn activates extrinsic apoptosis through binding to its cognate receptor in hepatocytes where transcription had been blocked by D-GalN (Ding et al. Dissection of the multiple mechanisms of TNF-alpha induced apoptosis in liver injury. J Cell Mol Med 2004; 8(4): 445-54; and Wullaert et al. Mechanisms of crosstalk between TNF-induced NF-kappaB and JNK activation in hepatocytes. Biochem Pharmacol 2006; 72(9): 1090-101). The protective effects of MSO were investigation to see if the effects were caused by inhibition of the apoptosis triggered by LPS/D-GalN in hepatocytes. Caspase-3 is a key apoptotic effector, both in intrinsic and in extrinsic apoptotic pathways, and it is activated downstream to engagement of TNF or Fas receptors. (Taylor et al. Apoptosis: controlled demolition at the cellular level. Nat Rev Mol Cell Biol 2008; 9(3): 231-41). Caspase-3 activation was measured as a hallmark of apoptosis induction in mouse liver extracts. FIG. 3A shows that, animal exposure to LPS/D-GalN for 5 hours elicits a marked caspase-3 activation, which is completely prevented by MSO pretreatment. MSO might act either downstream to TNFα binding to its cognate receptor, blunting some intracellular steps of apoptosis signaling; or upstream to TNF-R engagement, e.g. by inhibiting ligand production or delivery. FACS analyses were run on a cell model that closely resembles mouse hepatocytes, i.e. the mouse liver progenitor cells MLP-29. FIG. 3B shows that TNF-α induced apoptosis of MLP-29 cells, as displayed by the combined mitochondrial depolarization and plasma membrane loss of asymmetry and integrity; remarkably, neither MSO nor BSO could rescue cells from the noxious action of TNF-α. This experiment clearly states that the protective effect of MSO occurs prior to initiation of TNF-α signaling in hepatocytes. In accord with an inhibitory role of MSO at a point upstream of death receptor binding, MSO pretreatment had no effect on survival even when apoptosis was triggered in mice by induction of the Fas ligand pathway via the Jo2 anti-Fas agonist antibody (FIG. 3C). Actinomycin D was included to inhibit transcription, thus sensitizing cells to apoptosis induced by TNF-α, similarly to D-GalN in the in vivo experiments.

MSO inhibits the massive cytokine response seen in LPS/D-GalN treatment: One of the earliest effects of LPS/D-GalN administration is to trigger the release of pro-inflammatory cytokines. A mouse cytokine array was used to determine how MSO treatment affected plasma levels of 40 different cytokines following treatment of mice with LPS/D-GalN in order to draw a comprehensive picture of how MSO might be affecting the early immune response. These arrays to visualize the cytokine response in plasma collected one hour or three hours after LPS/D-GalN administration. FIG. 4 shows the cytokines seen in plasma drawn one and three hours after LPS/D-GalN administration with or without MSO treatment. Each blot represents the plasma from a single animal. Cytokine arrays were obtained from R&D Systems. Each membrane has 40 different mouse cytokines spotted in duplicate. The cytokines were identified using the column and lane number of each spot corresponding to the manufacturers table. Each membrane contained three positive and one negative control, each spotted in duplicate. Each blot represents the plasma cytokine profile from a single mouse. For FIG. 4, the two control blots, one of which is shown in FIG. 4A, were on plasma isolated from negative controls (overnight-starved animals not treated with MSO or LPS/D-GalN). The blots of plasma taken from two animals killed were analyzed three hours after LPS/D-GalN administration, one of which is shown in FIG. 4B. FIG. 4C shows one of the two blots of plasma from animals pretreated with MSO three hours prior to LPS/D-GalN injection. The locations of each of the 40 cytokines detectable in these blots are described in the online resource available at [www.rndsystems.com/pdf/ary006.pdf].

The results showed that, as expected, secretion of many of these cytokines is dramatically increased during ALF progression. Three hours after disease induction, 22 of the 40 cytokines are found to be elevated and 20 of these were reduced by MSO pretreatment. The results for 25 detected cytokines are summarized in FIG. 5A and FIG. 5B, and the major differences are described in the following paragraphs.

Cytokines C5a, sICAM-1, KC, M-CSF, and TIMP-1 were all detected on the control blots. In the one-hour samples from LPS/D-GalN-treated mice, only IL-6, KC, M-CSF, JE, MIP-2, TNF-α and TIMP-1 were elevated, and only IL-6 and TNF-α were reduced—both by >50%—in plasma from MSO-pretreated animals. These acute-phase cytokines initiate the downstream immune response which is seen in the three-hour cytokine blots shown in FIG. 4 and quantitated in FIG. 5A and FIG. 5B. Three hours after LPS/D-GalN treatment, both LPS/D-GalN treated animals and MSO-pretreated LPS/D-GalN treated animals showed a 10-20% reduction in C5a and sICAM. M-CSF values were the same for all three groups. KC and TIMP-1 signals were increased by more than 50% in LPS/D-GalN treated mice. KC values for MSO pre-treated values were same as in LPS/D-GalN animals; however, TIMP-1 values were reduced to approximately control values.

Induction of IFN-γ, IL-1ra, IL-6, IL-16, and IL-23 by LPS/D-GalN was abolished by MSO, whereas IL-1a level was reduced by more than 50%. Neutrophil-produced cytokines such as IP-10, I-TAC and MIG were all detected in plasma from LPS/D-GalN treated mice. IP-10 was reduced by more than 50% with MSO pretreatment and MIG and I-TAC were not detected. Macrophage-produced cytokines such as MIP-1a and MIP-1b, and chemokines such as JE and RANTES, which were elevated with LPS/D-GalN treatment, were either reduced or not detected with MSO pretreatment. The two exceptions were MCP-5 (monocyte chemotactic protein) and MIP-2 (macrophage inflammatory protein-2 gamma), both of which were increased in plasma from MSO-treated animals. Most importantly, TNF-α induction by LPS/D-GalN was abrogated by MSO pretreatment.

TNF-α and IFN-γ are secreted by different cells as part of the response to LPS administration, and both are seen in the cytokine arrays described above. TNF-α and IFN-γ activate separate apoptotic pathways. TNF-α activates cell death via the JNK pathway (Schwabe et al. Mechanisms of Liver Injury. I. TNF-alpha-induced liver injury: role of IKK, JNK, and ROS pathways. Am J Physiol Gastrointest Liver Physiol 2006; 290(4): G583-9) and IFN-γ activates apoptosis via the Jak-STAT1 pathway (Horvath, C M. The Jak-STAT pathway stimulated by interferon gamma. Sci STKE 2004; 2004 (260): tr8). To identify the effect of MSO on secretion of these two cytotoxic cytokines, the cytokine array studies were followed with ELISA analysis of plasma levels of TNF-α and IFN-γ. FIGS. 6A and 6B show ELISA assays carried out on plasma taken from individual mice killed either at t=0 (control animals—injected with MSO or saline for 3 hours, but not exposed to LPS/D-GalN) and at 1, 2, 3, 4, or 5 hours after LPS/D-GalN treatment. These are the same mice for which glutamine synthetase activities in liver extracts are shown in FIG. 2.

FIG. 6A shows that TNF-α was not detectable in plasma taken from t=0, control mice injected three hours previously with either MSO (n=7) or saline (n=7). For saline pretreated and LPS/D-GalN-treated animals, TNF-α levels peaked at one hour (mean: 590±91 SEM pg/ml) then dropped at later times. In contrast, MSO-pre-treated animals exhibit low TNF-α levels throughout the time course of experiment, never reaching 200 pg/ml (peak 1 hour time point mean: 112±35 SEM pg/ml). The p value for the difference between the saline-treated and the MSO-treated groups of mice at 1 hour is <0.001.

Another important cytokine whose expression is elicited by LPS is IFN-γ, which could contribute to apoptosis regulation via activation of the JAK/STAT pathway. FIG. 6B shows that LPS/D-GalN-treatment increases IFN-γ cytokine levels from 0.84±0.25 pg/ml at one hour to 41±11 pg/ml at 4 hours, and that MSO markedly inhibits this increase (0.19±0.05 pg/ml at 1 hour; 5.0±3.0 pg/ml at 4 hours). The p value for differences between the LPS/D-GalN and MSO treated groups of mice at 4 hour is 0.01.

An ELISA assays was also conducted to test the effect of MSO pretreatment on IL-6, another acute phase protein involved in orchestrating the early phases of the inflammatory response (Streetz et al. Mediators of inflammation and acute phase response in the liver. Cell Mol Biol (Noisy-legrand) 2001; 47(4): 661-73). IL-6 is secreted by macrophages in liver and along with TNF-α is a critical early mediator of immune signaling during disease progression. Low levels of IL-6 are hepatoprotective, and the resultant low levels of STAT3 activation are also hepatoprotective. As described above, IL-6, like TNF-α, is seen in the cytokine blots of both the one-hour and three-hour plasma samples from LPS/D-GalN treated mice. FIG. 6C shows that LPS/D-GalN treatment increases IL-6 from 166±41 pg/ml (mean±SEM) at one hour to 401±14 pg/ml (mean±SEM) at two hours. Thereafter it decreases gradually till 5 hours. The plasma from MSO pre-treated mice show low levels of IL-6, with a peak of (mean) 325±27 SEM pg/ml at 3 hours. The p value for the difference between the saline-treated and the MSO-treated groups of mice at 1 hour is <0.001.

The effects of IFN-γ as well as other IFNs, are mediated by its activation of the tyrosine kinases Jak1 and Jak2, which phosphorylate and activate the transcription factors of the STAT family. (Levy et al. Stats: transcriptional control and biological impact. Nat Rev Mol Cell Biol 2002; 3(9): 651-62). As this is the primary pathway for the activation of IFN-γ responsive genes we wished to determine if the reduction in IFN-γ seen with MSO was sufficient to affect this pathway. As can be seen in FIG. 7, LPS/D-GalN treatment leads to a large increase in STAT1 activation and this increase is eliminated in the presence of MSO. The effects of MSO treatment on activation of STAT2, 3, 5, and 6 were also tested. None showed effects as dramatic as those seen with STAT1, but phosphorylated STAT3 is decreased by MSO-treatment in both LPS/D-GalN treated and untreated mice.

Effects of MSO on in vitro production of TNF-α by peritoneal macrophages: Taken together, the data demonstrates that MSO exerts its protective function prior to apoptosis induction in hepatocytes, as it down-modulates cytokine induction following LPS exposure. Macrophages coordinate the early phases of LPS-induced inflammatory response, through the synthesis of TNF-α and other cytokines. In vitro experiments were conducted to directly test if MSO inhibits TNF-α production on LPS-stimulated macrophages obtained from mouse peritoneum. Macrophages were triggered with LPS with or without MSO, wherein the MSO was added either three hours before, one hour after, or at the same time as LPS. Four hours after LPS addition, TNF-α in the culture supernatant was quantitated by ELISA, as described in Methods. MSO resulted in a decrease in TNF-α in every one of six separate experiments. The average ELISA value for the LPS control was 527 pg/50 μL of culture medium. If MSO was added either three hours before LPS treatment, at the same time as LPS treatment, or one hour after LPS treatment, the average ELISA values were 393 pg/50 μL, 442 pg/50 μL, and 430 pg/50 μL, respectively. Therefore, depending upon the time of addition, the average reductions in TNF-α were between 16-25%. These decreases were significant, with 2-sided p values calculated by the dependent t test of 0.01, 0.002, and 0.04 depending on the time of addition of MSO. The reduction in TNF-α was not significantly affected by the time of addition. Trypan blue testing confirmed that there was no effect of MSO on cell viability over the time course of these experiments. This experiment verified that MSO can act directly on macrophages to inhibit cytokine production, despite the presence of 2 mM glutamine in the culture medium. The significance of MSO acting even in the presence of external glutamine is discussed below.

DISCUSSION

Treatment of mice with MSO alone three hours prior to inducing liver failure with LPS and D-GalN significantly increased survival. Subsequent analyses showed that MSO treatment prevented caspase-3 activation, indicating that this drug was affecting a stage upstream to cell death in the uncontrolled response which is primarily directed against the liver during ALF (Strasser et al. Apoptosis signaling. Annu Rev Biochem 2000; 69: 217-45; Leist et al. Four deaths and a funeral: from caspases to alternative mechanisms. Nat Rev Mol Cell Biol 2001; 2(8): 589-98; and Luan et al. Tolerance of mice to lipopolysaccharide is correlated with inhibition of caspase-3-mediated apoptosis in mouse liver cells. Acta Biochim Biophys Sin (Shanghai) 2007; 39(2): 96-100). Immunoblot analysis showed that MSO pretreatment reduced the production of several pro-inflammatory cytokines, and more sensitive ELISA studies showed that MSO suppressed the production of TNF-α and IFN-γ. TNF-α is an important acute phase protein whose production by macrophages and binding to the TNF-α receptor on hepatocytes activates a network of signal transduction pathways that regulate gene expression and cell death. When transcription is blocked, e.g. with D-GalN, pro-apoptotic pathways, including aggregation of a death-inducing signaling complex and activation of the stress kinase JNK, prevail and lead to a rapid cell dismantling. IFN-γ is produced in the liver by natural killer (NK) and NK T cells and is involved in the immune response against viral and bacterial infections by stimulating macrophages to produce more cytokines (Saha et al. Gene modulation and immunoregulatory roles of interferon gamma. Cytokine 2010; 50(1): 1-14). Moreover, IFN-γ is independently capable of initiating cell death by inducing the Jak-STAT pathway, and STAT1 activation is seen in the livers of LPS D-GalN treated mice. As seen in FIGS. 6A-6C, MSO treatment affects both the TNF-α and IFN-γ-dependent pathways, but the suppressive effect of MSO treatment on TNF-α and IFN-γ production also involves a larger suppression of cellular immunity, since MSO treatment affects the levels of other macrophage secreted cytokines such as MIG, MIP-la, MIP-1b, and MCF in plasma drawn 3 hours after disease induction. Most of these cytokines were either absent or reduced by more than 50% in the plasma from MSO pre-treated mice. MSO is an inhibitor of both glutamine synthetase and γ glutamyl cysteine synthetase, but at the dose used it inhibited only glutamine synthetase.

The simplest explanation for the ability of MSO to alter the immune response initiated by LPS/D-GalN is that changes in glutamine concentration, either in the plasma or in immune cells, affect the activation of immune cells, most likely peritoneal macrophages or Kupffer cells, since these cells are the earliest producers of TNF-α after an i.p. administration of LPS. It is known in the art that glutamine levels influence macrophage function and cytokine release in tissue culture, and long-term dietary changes can modify immune function in living animals (Newsholme, P. Why is L-glutamine metabolism important to cells of the immune system in health, postinjury, surgery or infection? J Nutr 2001; 131(9 Suppl): 2515S-22S; discussion 23S-4S; Li et al. Amino acids and immune function. Br J Nutr 2007; 98(2): 237-52; and ROTH E. Immune and cell modulation by amino acids. Clin Nutr 2007; 26(5): 535-44). The action of MSO on glutamine synthetase may be lowering plasma glutamine and thereby changing the global anabolic response to infection. In vitro, lowered glutamine leads to decreased proliferation in mitogen-stimulated lymphocytes and impairs the differentiation of plasma cells (Crawford et al. The essential role of L-glutamine in lymphocyte differentiation in vitro. J Cell Physiol 1985; 124(2): 275-82; and Szondy et al. The effect of glutamine concentration on the activity of carbamoyl-phosphate synthase II and on the incorporation of [3H]thymidine into DNA in rat mesenteric lymphocytes stimulated by phytohaemagglutinin. Biochem J 1989; 261(3): 979-83). The reduction in glutamine seen after severe burns may also be responsible for the impaired immune response seen in this and other stress conditions (Kew et al. Dietary glutamine enhances murine T-lymphocyte responsiveness. J Nutr 1999; 129(8): 1524-31). Again in vitro, a detailed study of the effect of glutamine concentrations on T cell differentiation divided the response into an early and glutamine-independent phase and a latter glutamine dependent phase (Horig et al. Exogenous glutamine requirement is confined to late events of T cell activation. J Cell Biochem 1993; 53(4): 343-51). Finally, dietary glutamine enhances cytokine production in macrophages and increases T cell responsiveness (Rogero et al. Dietary glutamine supplementation increases the activity of peritoneal macrophages and hemopoiesis in early-weaned mice inoculated with *Mycobacterium bovis bacillus* Calmette-Guerin. J Nutr 2008; 138(7): 1343-8).

It has been shown that tissue-macrophage depletion improves survival in mice challenged with LPS/D-GalN (Emoto et al. Increased resistance of LFA-1-deficient mice to lipopolysaccharide-induced shock/liver injury in the presence of TNF-alpha and IL-12 is mediated by IL-10: a novel role for LFA-1 in the regulation of the pro-inflammatory and anti-inflammatory cytokine balance. J Immunol 2003; 171 (2): 584-93), and that transfer of macrophages derived from bone-marrow precursor cells from wild type mice into TL4R-mutant mice is sufficient to confer susceptibility to LPS/D-GalN-induced lethality (Freudenberg et al. Requirement for lipopolysaccharide-responsive macrophages in galactosamine-induced sensitization to endotoxin. Infect Immun 1986; 51(3): 891-5), but the relative importance of peritoneal macrophages in the lethality caused by LPS/D-GalN is not known. The conventional view is that, given the large mass of Kupffer cells and their close proximity to hepatocytes, their secretion of TNF-α and other cytokines is the proximate cause of death (Ide et al. Effects of gadolinium chloride (GdCl(3)) on the appearance of macrophage populations and fibrogenesis in thioacetamide-induced rat hepatic lesions. J Comp Pathol 2005; 133(2-3):92-102; Luster et al. Endotoxin-induced cytokine gene expression and excretion in the liver. Hepatology 1994; 19(2): 480-8; and Tacke et al Inflammatory pathways in liver homeostasis and liver injury. Clin Rev Allergy Immunol 2009; 36(1): 4-12). Since inhibiting glutamine synthetase can affect cell death, MSO might be inhibiting Kupffer cell response by either decreasing the external concentration of plasma glutamine in the vicinity of Kupffer cells, or by directly inhibiting cellular glutamine synthetase for peritoneal macrophages treated with MSO in vitro. The fact that treatment of isolated peritoneal macrophages with 9 mM MSO in the presence of 2 mM glutamine significantly reduces TNF-α indicates that even in the presence of external glutamine, peritoneal macrophage glutamine synthetase is still required for maximal TNF-α synthesis and/or secretion. But since Kupffer cells are likely to have the major role in the production of TNF-α additional and more complex experiments will be needed to determine if the inhibition of glutamine synthetase in these liver-resident macrophages is sufficient to account for the striking diminution of the immune response observed.

However, studies of the in vitro effects of glutamine on isolated systems of immune cells are inadequate for understanding the complex events occurring with LPS/D-GalN stimulation. An i.p. injection of 50 mg/kg MSO lowers plasma glutamine concentrations by about 50% (in preparation). Under long term MSO treatment, plasma glutamine levels return to normal even though glutamine synthetase in the liver remains inhibited by 90%, presumably due to the large amounts of glutamine present in the standard mouse diet. In any case, plasma glutamine levels might be of minimal importance in the context of macrophage activation in the liver, where the local production of glutamine by glutamine synthetase may influence the external concentration seen by Kupffer cells. As blood in the liver flows from the portal to the venous side, glutamine concentrations change. The periportal cells actively transport glutamine, concentrating it by 10-fold (Haussinger et al. Interactions between glutamine metabolism and cell-volume regulation in perfused rat liver. Eur J Biochem 1990; 188(3): 689-95; and Labow et al. Glutamine. World J Surg 2000; 24(12): 1503-13). This removal of glutamine is central to liver function since it is converted by liver glutaminase into urea and glutamate, controlling blood ammonia levels through its incorporation into urea. Both glutamate and urea are transported back into the periportal blood. As the glutamate-enriched and glutamine depleted blood reaches the perivenous side of the liver, glutamate is transported into the perivenous cells and used by glutamine synthetase to make glutamine, which is then available to Kupffer cells associated with the perivenous hepatocytes. Perivenous hepatocytes, while constituting only 5% of the hepatoocyte population are the only liver cells containing glutamine synthetase (Gebhardt et al. Heterogeneous distribution of glutamine synthetase among rat liver parenchymal cells in situ and in primary culture. EMBO J 1983; 2(4): 567-70; and Haussinger et al. Hepatocyte heterogeneity in glutamate metabolism and bidirectional transport in perfused rat liver. Eur J Biochem 1989; 185(1): 189-95). There are two populations of Kupffer cells as distinguished by morphology, function, and location. The Kupffer cells at the periportal side are more active in phagocytosis while those at the perivenous side respond much more strongly to LPS (Bykov et al. Functional Differences between Periportal and Perivenous Kupffer Cells Isolated by Digitonin-Collagenase Perfusion. Comp Hepatol 2004; 3 Suppl 1: S34; Sleyster et al. Relation between localization and function of rat liver Kupffer cells. Lab Invest 1982; 47(5): 484-90; Armbrust et al. Functional characterization of two different Kupffer cell populations of normal rat liver. J Hepatol 1996; 25(4): 518-28; and Hoedemakers et al. Heterogeneity in secretory responses of rat liver macrophages of different size. Liver 1995; 15(6): 313-9). As noted above, it is clear that glutamine is required for the activation of immune cells. The results suggest that the immunologically reactive Kupffer macrophages may be dependent upon the glutamine synthesized specifically by perivenous hepatocytes. The inhibition of glutamine synthetase in this population by MSO could reduce the response to LPS/D-GalN, independent of any changes in plasma levels of glutamine.

An additional mechanism independent of plasma glutamine levels may also be involved. As shown in this report, MSO is also able to reduce TNF-α secretion in isolated peritoneal macrophages even in the presence of 2 mM glutamine, implying that the macrophage glutamine synthetase is directly involved in the synthesis and/or secretion of TNF-α. Finally, inhibition of glutamine synthetase by MSO may reduce internal glutamine in immune cells and thereby interfere with energy generation or another critical biochemical processes required for activation. For example, mTOR activation requires an internal pool of glutamine and the critical size of this pool may be altered by the inhibition of glutamine synthetase by MSO (Nicklin et al. Bidirectional transport of amino acids regulates mTOR and autophagy. Cell 2009; 136(3): 521-34). Liver tumor cells often have high levels of glutamine synthetase and presumably internal glutamine, priming them for proliferation (Apte et al. Beta-catenin activation promotes liver regeneration after acetaminophen-induced injury. Am J Pathol 2009; 175(3): 1056-65). In addition, the synthesis of glutamine synthetase is under the control of the Wnt/β-catenin signaling pathway with β-catenin required for three enzymes involved in glutamine metabolism, including glutamine synthetase (Sekine et al. Liver-specific loss of beta-catenin blocks glutamine synthesis pathway activity and cytochrome p450 expression in mice. Hepatology 2006; 43(4): 817-25), again suggesting that glutamine plays a central role in hepatocyte metabolism.

Although there is abundant data showing that glutamine is essential for the proper functioning of immune cells, there is also abundant data showing that in the case of a harmful inflammatory response, added glutamine is beneficial. Weitzel and Wischmeyer (Crit Care Clin 26 (2010) 515-525) have reviewed the literature and shown that the preponderance of studies on the effects of glutamine or glutamine treatment on inflammation show that glutamine is beneficial. From those studies, it would therefore be completely unexpected that the inhibition of glutamine synthetase by MSO would be beneficial in inflammatory diseases.

In conclusion, MSO, a well-characterized mechanism-based inhibitor of glutamine synthetase and other enzymes, has a striking and unexpected effect of increasing survival in the LPS/D-GalN mouse model for ALF. It prevents the activation of caspase-3 and furthermore significantly reduces the overall inflammatory immune response as measured by reductions in the levels of plasma cytokines, and it prevents the ensuing activation of caspase-3 and apoptosis induction in hepatocytes. Of particular interest is that levels of TNF-α and IL6 are reduced one hour after LPS/D-GalN treatment, indicating that the primary target of MSO is some step very early in the immune response, most likely in the alteration of macrophage/Kupffer cell activation.

The examples and other embodiments described herein are exemplary and not intended to be limiting in describing the full scope of compositions and methods of this technology. Equivalent changes, modifications and variations of specific embodiments, materials, compositions and methods may be made within the scope of the present technology, with substantially similar results.

Non-Limiting Discussion of Terminology

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition or method.

The citation of references herein does not constitute an admission that those references are prior art or have any relevance to the patentability of the technology disclosed herein. All references cited in the Description section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the word "desired" refers to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters.

What is claimed is:

1. A method for treating acute pancreatitis in a human or a subject comprising administering to the subject a safe and effective amount of methionine sulfoximine (MSO).

2. The method according to claim 1, wherein the MSO is selected from the group consisting of L-methionine S-sulfoximine, L-methionine R-sulfoximine, and mixtures thereof.

3. A method according to claim 2, wherein the MSO is a substantially pure enantiomer.

4. The method according to claim 2, wherein the MSO is a racemic mixture.

5. The method according to claim 1, wherein the administering of MSO is in a pharmaceutically carrier suitable for oral, intravenous or subcutaneous administration.

6. The method according to claim 1, wherein the administering of MSO is at a level of less than or about 5 mg/kg.

7. A method for treating acute pancreatitis in a human or a subject comprising administering to the subject a safe and effective amount of methionine sulfoximine (MSO), wherein the acute pancreatitis involves an aberrant immune response that destroys the subject's own cells.

8. The method of claim 7, wherein the acute pancreatitis is associated with the release of TNF-α and other cytokines in response to bacterial infection, viral infection or chemical poisoning.

9. The method according to claim 7, wherein the MSO is selected from the group consisting of L-methionine S-sulfoximine, L-methionine R-sulfoximine, and mixtures thereof.

10. A method according to claim 9, wherein the MSO is a substantially pure diastereomer.

11. The method according to claim 9, wherein the MSO is a diastereomeric mixture.

12. The method according to claim 7, wherein the administering of MSO is in a pharmaceutically carrier suitable for oral, intravenous or subcutaneous administration.

13. The method according to claim 7, wherein the administering of MSO is at a level of less than or about 8 mg/kg.

14. The method of claim 13, wherein the level is less than about 5 mg/kg.

15. The method of claim 14, wherein the level is less than about 2.5 mg/kg.

16. The method according to claim 1, wherein the administering of MSO is at a level of less than or about 8 mg/kg.

17. The method of claim 6, wherein the level is less than about 2.5 mg/kg.

* * * * *